(12) United States Patent
Weikel et al.

(10) Patent No.: US 6,679,886 B2
(45) Date of Patent: Jan. 20, 2004

(54) TOOLS AND METHODS FOR CREATING CAVITIES IN BONE

(75) Inventors: Stuart Weikel, Drexel Hill, PA (US); Nisra Thongpreda, Exton, PA (US); Mike Lehmicke, Havertown, PA (US); Douglas Kephart, Glen Mills, PA (US); Larry Binder, Langhorne, PA (US)

(73) Assignee: Synthes (USA), Paoli, PA (US)

( * ) Notice: Subject to any disclaimer, the term of this patent is extended or adjusted under 35 U.S.C. 154(b) by 67 days.

(21) Appl. No.: 09/939,759

(22) Filed: Aug. 28, 2001

(65) Prior Publication Data

US 2002/0032447 A1 Mar. 14, 2002

Related U.S. Application Data

(60) Provisional application No. 60/229,303, filed on Sep. 1, 2000.

(51) Int. Cl.[7] .............................................. A61B 17/32
(52) U.S. Cl. ........................... 606/79; 606/83; 606/167
(58) Field of Search ................ 606/79, 80, 81, 606/83, 84, 86, 167, 170, 171, 180

(56) References Cited

U.S. PATENT DOCUMENTS

| | | |
|---|---|---|
| 1,867,624 A | 7/1932 | Hoffman |
| 2,426,535 A | 8/1947 | Turkel ............................ 128/2 |
| 2,537,070 A | 1/1951 | Longfellow ................... 128/92 |
| 2,543,780 A | 3/1951 | Hipps et al. .................. 128/83 |
| 2,668,537 A | 2/1954 | Kapp .......................... 128/318 |
| 2,919,692 A | 1/1960 | Ackerman ...................... 128/2 |
| 3,030,951 A | 4/1962 | Mandarino .................... 128/92 |
| 3,112,743 A | 12/1963 | Cochran et al. .............. 128/92 |
| 3,176,395 A | 4/1965 | Warner et al. ................ 30/154 |
| 3,517,128 A | 6/1970 | Hines .......................... 128/345 |
| 3,598,108 A | 8/1971 | Jamshidi et al. ............. 128/2 B |
| 3,678,934 A | 7/1972 | Warfield et al. ............. 128/317 |
| 3,721,245 A | 3/1973 | Campbell .................... 128/318 |
| 3,915,169 A | 10/1975 | McGuire ..................... 128/305 |
| 4,007,743 A | 2/1977 | Blake ....................... 128/334 R |
| 4,203,444 A | 5/1980 | Bonnell et al. ............. 128/276 |
| 4,239,036 A | 12/1980 | Krieger ........................ 128/20 |
| 4,274,414 A | 6/1981 | Johnson et al. ............. 128/305 |
| 4,277,184 A | 7/1981 | Solomon ..................... 366/150 |
| 4,306,570 A | 12/1981 | Matthews .................... 128/754 |
| 4,543,966 A | 10/1985 | Islam et al. ................. 128/754 |
| 4,576,152 A | 3/1986 | Müller et al. ............. 128/92 R |
| 4,643,190 A | 2/1987 | Heimberger ................ 128/321 |

(List continued on next page.)

FOREIGN PATENT DOCUMENTS

| | | |
|---|---|---|
| DE | 3630069 C1 | 1/1988 |
| SU | 980703 | 12/1982 |
| SU | 990220 | 1/1983 |

(List continued on next page.)

OTHER PUBLICATIONS

A. Gangi et al., "Percutaneous Vertebroplasty Guided by a Combination of CT and Fluoroscopy," *AJNR*, vol. 15, pp. 83–86, Jan., 1994.

*Primary Examiner*—Pedro Philogene
(74) *Attorney, Agent, or Firm*—Pennie & Edmonds LLP

(57) ABSTRACT

Tools for use in the creation of cavities in bones. The tools include a probe, a cannula that provides percutaneous passageway to the interior of the treated bone, a bone tamp, and a system for delivering bone filler material into the cavity. The bone tamp has a shaft that is inserted into the bone through the cannula. The end of the shaft that is inserted into the bone may have a flapper tip that extends out of axial alignment with the shaft upon deployment by the physician. Once the tip is deployed, the bone tamp can be rotated to form the cavity. The cavity may then be treated with a medicament, filled with bone filler material, or both. Other tools and materials described herein may be used to lift or restore the treated bone closer to its natural anatomy.

31 Claims, 37 Drawing Sheets

U.S. PATENT DOCUMENTS

| | | | | |
|---|---|---|---|---|
| 4,653,489 | A | 3/1987 | Tronzo | 128/92 YV |
| 4,672,964 | A | 6/1987 | Dee et al. | 128/305 |
| 4,712,546 | A | 12/1987 | Noe | 128/305 |
| 4,770,174 | A | 9/1988 | Luckman et al. | 128/318 |
| 4,788,976 | A | 12/1988 | Dee | 128/305 |
| 4,842,578 | A | 6/1989 | Johnson et al. | 604/22 |
| 4,919,153 | A | 4/1990 | Chin | 606/93 |
| 4,944,744 | A | 7/1990 | Ray | 606/79 |
| 4,945,920 | A | 8/1990 | Clossick | 128/751 |
| 4,969,888 | A | 11/1990 | Scholten et al. | 606/94 |
| 4,983,179 | A | 1/1991 | Sjostrom | 606/180 |
| 5,002,543 | A | 3/1991 | Bradshaw et al. | 606/62 |
| 5,009,661 | A | 4/1991 | Michelson | 606/170 |
| 5,013,318 | A | 5/1991 | Spranza, III | 606/102 |
| 5,015,252 | A | 5/1991 | Jones | 606/205 |
| 5,015,255 | A | 5/1991 | Kuslich et al. | 623/17 |
| 5,041,119 | A | 8/1991 | Frigg et al. | 606/96 |
| 5,055,106 | A | 10/1991 | Lundgren | 606/167 |
| 5,059,193 | A | 10/1991 | Kuslich | 606/61 |
| 5,062,845 | A | 11/1991 | Kuslich et al. | 606/80 |
| 5,084,050 | A | 1/1992 | Draenert | 606/77 |
| 5,108,404 | A | 4/1992 | Scholten et al. | 606/94 |
| 5,112,346 | A | 5/1992 | Hiltebrandt et al. | 606/170 |
| 5,113,846 | A | 5/1992 | Hiltebrandt et al. | 128/20 |
| 5,137,514 | A | 8/1992 | Ryan | 604/99 |
| 5,156,606 | A | 10/1992 | Chin | 606/86 |
| 5,171,248 | A | 12/1992 | Ellis | 606/102 |
| 5,174,300 | A | 12/1992 | Bales et al. | 128/751 |
| 5,183,466 | A | 2/1993 | Movern | 604/110 |
| 5,201,741 | A | 4/1993 | Dulebohn | 606/113 |
| 5,209,747 | A | 5/1993 | Knoepfler | 606/16 |
| 5,275,608 | A * | 1/1994 | Forman et al. | 606/170 |
| 5,307,805 | A | 5/1994 | Byrne | 128/20 |
| 5,314,445 | A | 5/1994 | Heidmueller nee Degwitz et al. | 606/208 |
| 5,318,528 | A | 6/1994 | Heaven et al. | 604/95 |
| 5,330,502 | A | 7/1994 | Hassler et al. | 606/205 |
| 5,339,802 | A | 8/1994 | Cook | 128/20 |
| 5,350,391 | A | 9/1994 | Iacovelli | 606/170 |
| 5,354,311 | A | 10/1994 | Kambin et al. | 606/205 |
| 5,374,269 | A | 12/1994 | Rosenberg | 606/80 |
| 5,376,094 | A | 12/1994 | Kline | 606/113 |
| 5,376,100 | A | 12/1994 | Lefebvre | 606/180 |
| 5,383,888 | A | 1/1995 | Zvenyatsky et al. | 606/206 |
| 5,390,683 | A | 2/1995 | Pisharodi | 128/898 |
| 5,411,514 | A | 5/1995 | Fucci et al. | 606/180 |
| 5,423,824 | A | 6/1995 | Akerfeldt et al. | 606/80 |
| 5,431,671 | A | 7/1995 | Nallakrishnan | 606/167 |
| 5,443,475 | A | 8/1995 | Auerbach et al. | 606/170 |
| 5,445,639 | A | 8/1995 | Kuslich et al. | 606/80 |
| 5,454,365 | A | 10/1995 | Bonutti | 600/204 |
| 5,467,763 | A | 11/1995 | McMahon et al. | 600/201 |
| 5,474,571 | A | 12/1995 | Lang | 606/205 |
| 5,487,745 | A | 1/1996 | McKenzie | 606/83 |
| 5,490,852 | A | 2/1996 | Azer et al. | 606/79 |
| 5,507,773 | A | 4/1996 | Huitema et al. | 606/170 |
| 5,512,037 | A | 4/1996 | Russell et al. | 600/206 |
| 5,514,137 | A | 5/1996 | Coutts | 606/62 |
| 5,514,157 | A | 5/1996 | Nicholas et al. | 606/206 |
| 5,540,706 | A | 7/1996 | Aust et al. | 606/170 |
| 5,549,637 | A * | 8/1996 | Crainich | 606/207 |
| 5,556,429 | A | 9/1996 | Felt | 623/16 |
| 5,562,665 | A | 10/1996 | Young | 606/62 |
| 5,571,109 | A | 11/1996 | Bertagnoli | 606/61 |
| 5,571,131 | A | 11/1996 | Ek et al. | 606/184 |
| 5,586,990 | A | 12/1996 | Hahnen et al. | 606/170 |
| 5,637,112 | A | 6/1997 | Moore et al. | 606/148 |
| 5,649,947 | A | 7/1997 | Auerbach et al. | 606/170 |
| 5,649,957 | A | 7/1997 | Levin | 606/207 |
| 5,662,676 | A | 9/1997 | Koninckx | 606/198 |
| 5,674,224 | A | 10/1997 | Howell et al. | 606/88 |
| 5,676,678 | A | 10/1997 | Schad | 606/170 |
| 5,702,408 | A | 12/1997 | Wales et al. | 606/139 |
| 5,709,697 | A | 1/1998 | Ratcliff et al. | 606/180 |
| 5,741,261 | A | 4/1998 | Moskovitz et al. | 606/79 |
| 5,755,723 | A * | 5/1998 | Lombardo | 606/170 |
| 5,788,703 | A | 8/1998 | Mittelmeier et al. | 606/94 |
| 5,797,923 | A | 8/1998 | Aiyar et al. | 606/129 |
| 5,800,437 | A | 9/1998 | Gustilo et al. | 606/86 |
| 5,800,450 | A | 9/1998 | Lary et al. | 606/180 |
| 5,810,826 | A | 9/1998 | Akerfeldt et al. | 606/80 |
| 5,810,876 | A | 9/1998 | Kelleher | 606/205 |
| 5,827,289 | A | 10/1998 | Reiley et al. | 606/86 |
| 5,827,304 | A | 10/1998 | Hart | 606/159 |
| 5,833,692 | A | 11/1998 | Cesarini et al. | 606/79 |
| 5,855,565 | A | 1/1999 | Bar-Cohen et al. | 604/104 |
| 5,867,912 | A | 2/1999 | Hickok et al. | 30/329 |
| 5,879,353 | A | 3/1999 | Terry | 606/85 |
| 5,885,258 | A | 3/1999 | Sachdeva et al. | 604/281 |
| 5,891,153 | A | 4/1999 | Peterson | 606/107 |
| 5,893,835 | A | 4/1999 | Witt et al. | 601/2 |
| 5,895,398 | A | 4/1999 | Wensel et al. | 606/159 |
| 5,908,432 | A | 6/1999 | Pan | 606/167 |
| 5,928,239 | A * | 7/1999 | Mirza | 606/79 |
| 5,938,678 | A * | 8/1999 | Zirps et al. | 606/170 |
| 5,944,730 | A | 8/1999 | Nobles et al. | 606/151 |
| 5,957,925 | A | 9/1999 | Cook et al. | 606/87 |
| 5,964,770 | A | 10/1999 | Flomenblit et al. | 606/78 |
| 5,968,053 | A | 10/1999 | Revelas | 606/108 |
| 5,968,078 | A | 10/1999 | Grotz | 606/232 |
| 5,972,015 | A | 10/1999 | Scribner et al. | 606/192 |
| 5,989,260 | A | 11/1999 | Yao | 606/102 |
| 5,989,277 | A | 11/1999 | LeMaire, III et al. | 606/170 |
| 6,030,406 | A | 2/2000 | Davis et al. | 606/198 |
| 6,048,346 | A | 4/2000 | Reiley et al. | 606/92 |
| 6,066,153 | A | 5/2000 | Lev | 606/180 |
| 6,071,308 | A | 6/2000 | Ballou et al. | 623/1.15 |
| 6,077,286 | A | 6/2000 | Cuschieri et al. | 606/170 |
| 6,113,617 | A | 9/2000 | van der Merwe | 606/167 |
| 6,126,664 | A | 10/2000 | Troxell et al. | 606/84 |
| 6,224,604 | B1 | 5/2001 | Suddaby | 606/80 |
| 6,241,734 | B1 * | 6/2001 | Scribner et al. | 606/93 |
| 6,287,313 | B1 | 9/2001 | Sasso | 606/96 |
| 6,383,188 | B2 | 5/2002 | Kuslich et al. | 606/80 |
| 6,395,007 | B1 | 5/2002 | Bhatnagar et al. | 606/94 |
| 6,440,138 | B1 | 8/2002 | Reiley et al. | 606/79 |
| 6,468,279 | B1 | 10/2002 | Reo | 606/79 |
| 2001/0034527 | A1 | 10/2001 | Scribner et al. | 606/93 |
| 2002/0022856 | A1 | 2/2002 | Johnson et al. | 606/185 |
| 2002/0068974 | A1 | 6/2002 | Kuslich et al. | 623/17.11 |
| 2002/0161373 | A1 | 10/2002 | Osorio et al. | 606/86 |
| 2002/0169471 | A1 | 11/2002 | Ferdinand | 606/185 |
| 2002/0188299 | A1 | 12/2002 | Reiley et al. | 606/79 |
| 2003/0004530 | A1 | 1/2003 | Reo | 606/185 |

FOREIGN PATENT DOCUMENTS

| | | |
|---|---|---|
| WO | WO 98/56301 | 12/1998 |
| WO | WO 99/18865 | 4/1999 |
| WO | WO 99/18866 | 4/1999 |
| WO | WO 99/47055 | 9/1999 |
| WO | WO 99/51149 | 10/1999 |
| WO | WO 01/30248 A1 | 5/2001 |
| WO | WO 01/30264 A2 | 5/2001 |
| WO | WO 01/76514 A2 | 10/2001 |

* cited by examiner

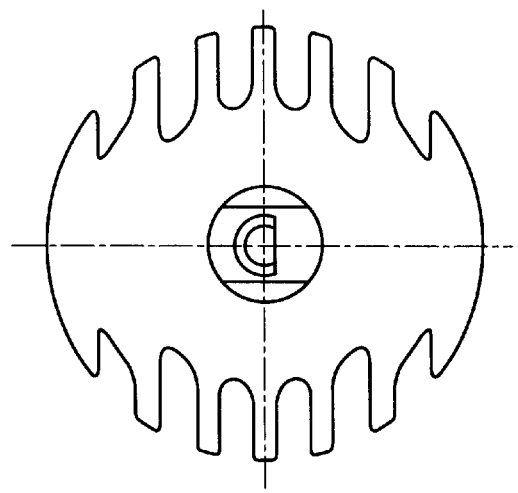
Fig. 4B
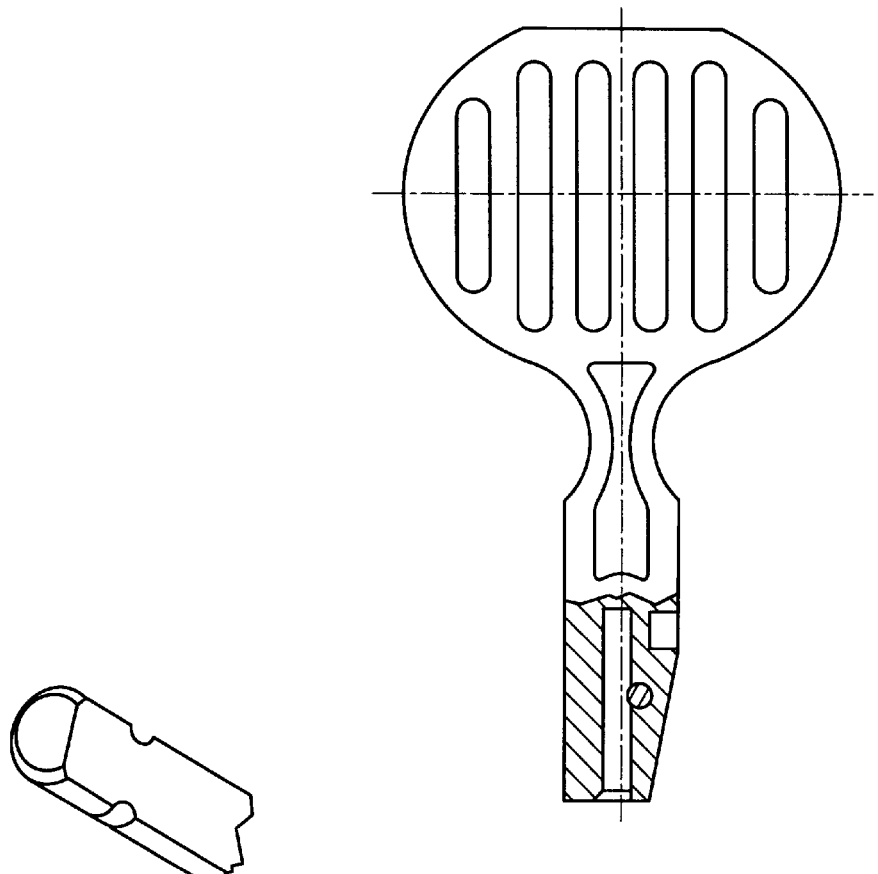
Fig. 4A
Fig. 4C

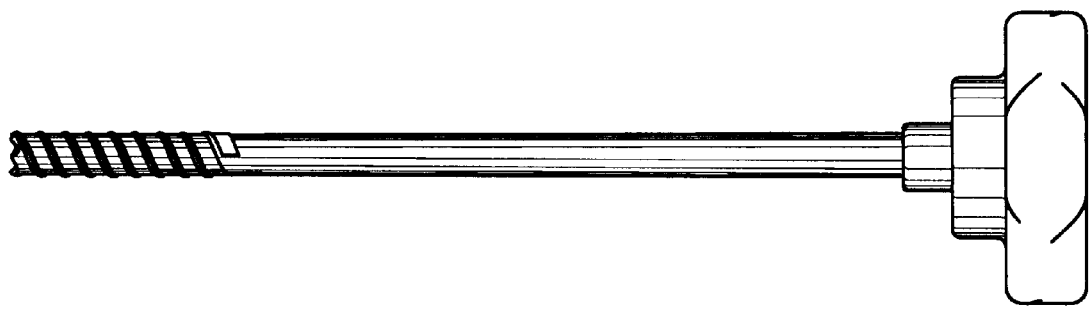
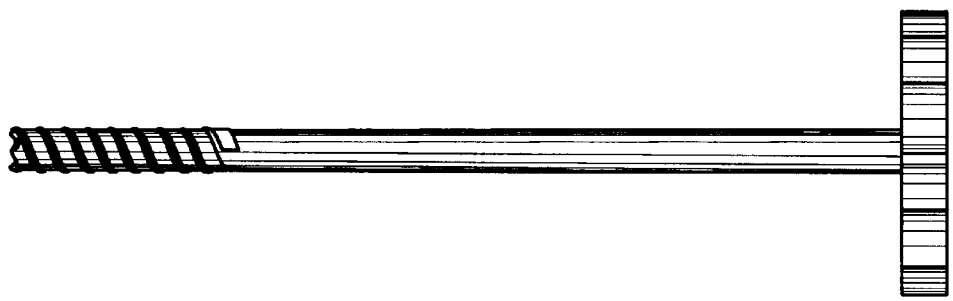
Fig. 5B

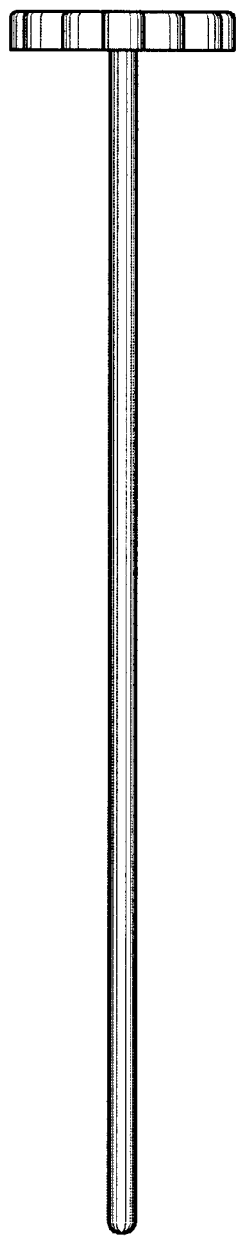
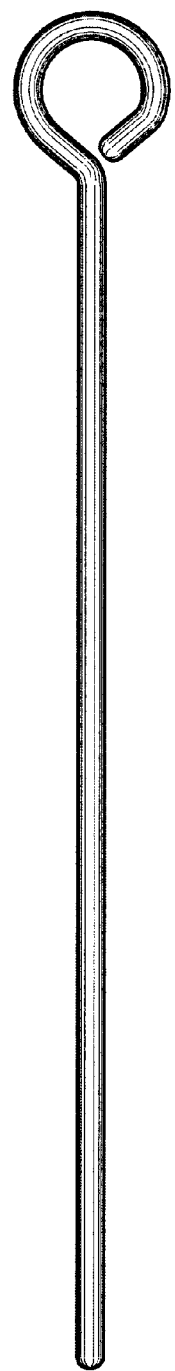
Fig. 8A                    Fig. 8B

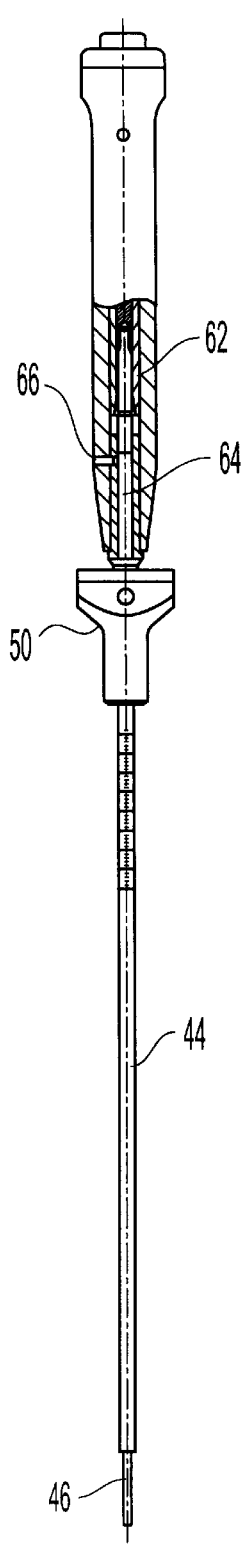
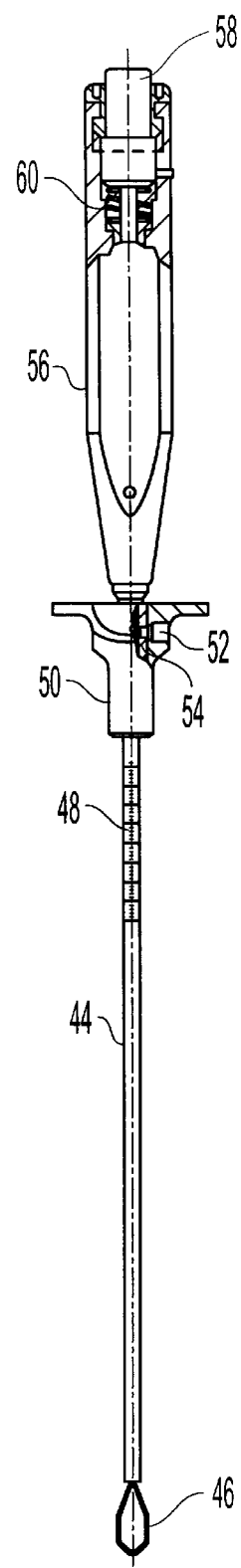
*Fig. 9A*                *Fig. 9B*

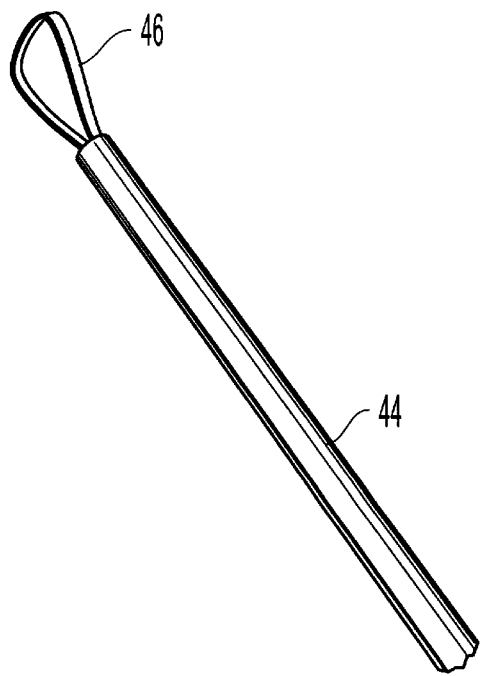
*Fig. 10C*
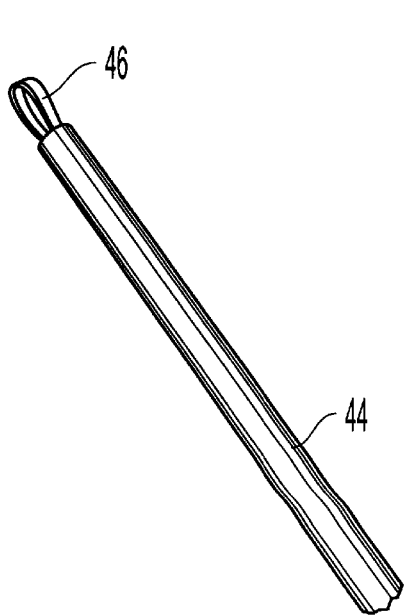 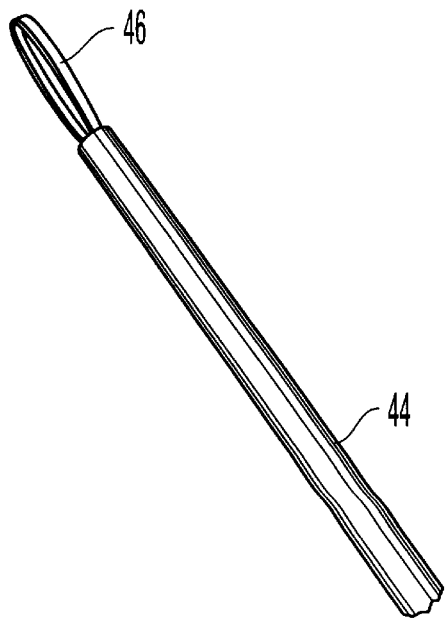
*Fig. 10A*  *Fig. 10B*

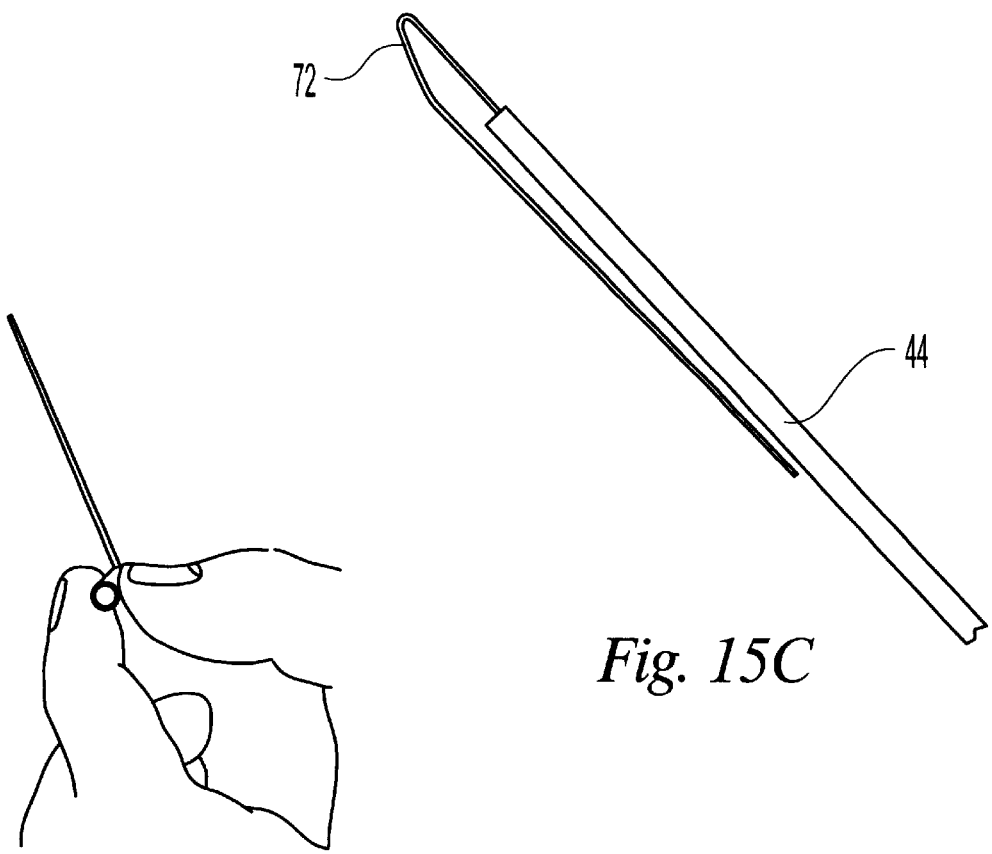
*Fig. 15C*
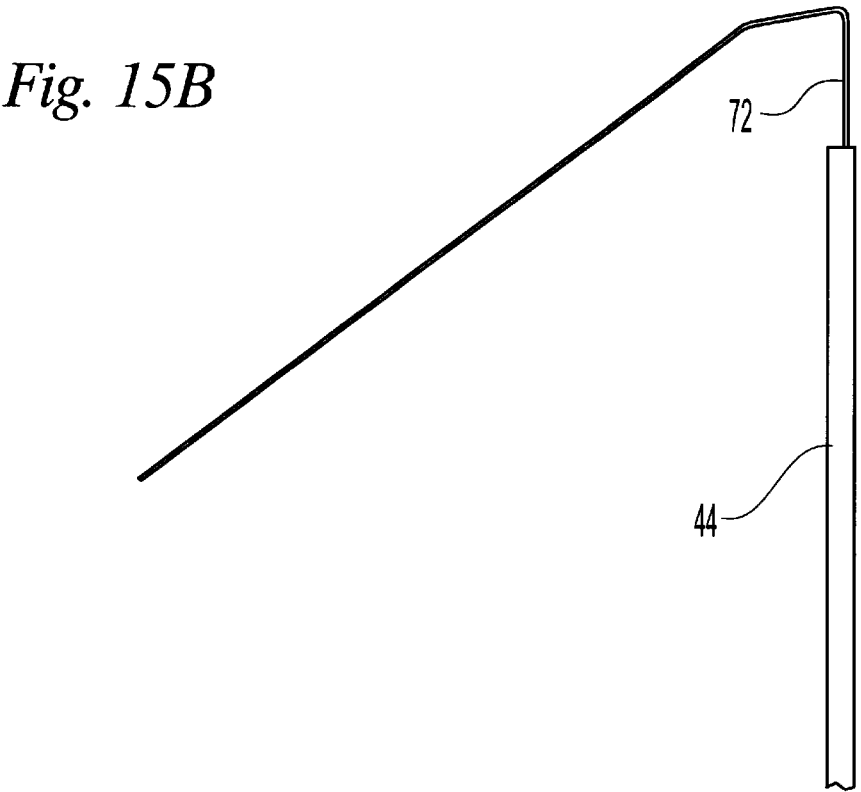
*Fig. 15B*
*Fig. 15A*

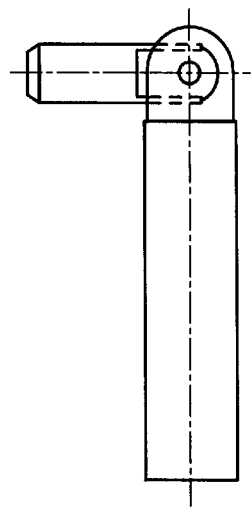
*Fig. 18E*
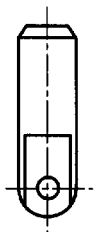 
*Fig. 18D*   *Fig. 18C*
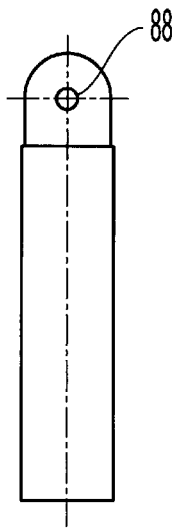 
*Fig. 18B*   *Fig. 18A*

TOOLS AND METHODS FOR CREATING CAVITIES IN BONE

This application claims the benefit of Provisional Application No. 60/229,303, filed Sep. 1, 2000.

FIELD OF THE INVENTION

The invention relates to tools and procedures, which, in use, form cavities in interior body regions of bones, particularly in vertebrae, for diagnostic or therapeutic purposes.

BACKGROUND OF THE INVENTION

Certain diagnostic or therapeutic procedures require the formation of a cavity in a bone mass. This procedure can be used to treat any bone, for example, bone which due to osteoporosis, avascular necrosis, cancer, or trauma, is fractured or is prone to compression fracture or collapse. These conditions, if not successfully treated, can result in deformities, chronic complications, and an overall adverse impact upon the quality of life.

For example, as described in U.S. Pat. Nos. 4,969,888, 5,108,404, and 5,827,389, an expandable body is deployed to form a cavity in cancellous bone tissue, as part of a therapeutic procedure that fixes fractures or other abnormal bone conditions, both osteoporotic and non-osteoporotic in origin. The expandable body compresses the cancellous bone to form an interior cavity. The cavity receives a filling material, which provides renewed interior structural support for cortical bone.

U.S. Pat. No. 5,062,845 described a surgical tool for preparing a graft site between opposing vertebra. The tool has a distal end with external dimensions sized to be passed through the patient's anatomy to a point of entry on the spine. At each incremental extension, the surgeon rotates the handle so that the blades cut out a large chamber equal to the size of the diameter of the extended extendable blades located on the distal end of the tool. After each such cut, the handle is turned to progressively increase the diameter of the cutting edges of blades until a chamber of desired size (up to the diameter of the fully extended blades) is formed. Intermittently, between enlarging the diameter of the cavity, the surgeon may retract the blades and remove the tool to flush the cavity being formed.

U.S. Pat. No. 5,512,037 describes a percutaneous surgical retractor having an outer sleeve with an open beveled configuration and having an angle defining a leading edge on the distal end of the outer sleeve to facilitate percutaneous insertion of the retractor; a blade slidable within said outer sleeve between at least a deployed position extending beyond the distal end of the outer sleeve and a retracted position disposed within the outer sleeve, the blade having a deployable memory curved distal end.

SUMMARY OF THE INVENTION

The invention provides new tools and methods for creating cavities in cancellous bone, for example but not limited to vertebroplasty, and for treating these cavities by injecting appropriate treatment materials, i.e., bone paste, cement, autograft, allograft, etc. The tools include a probe that introduces a passageway to the cancellous area, a cannula which expands the hole in the bone and provides a passageway for a tamp or flexible curette to push or tamp back the cancellous structure to form the cavity, and a syringe which fills the cavity with appropriate treatment material. These tools advantageously work together.

The Probe:

The probe is a long slender body with a sharp tip and a handle. The outer diameter of the long slender body is sufficient to fit inside the cannula. The tip of the probe may contain a drilling tip, a sharp point, a serrated edge, or a combination thereof. In a preferred embodiment, the probe has a changeable sharp tip firmly held by a probe sheath that provides strength and gently sloping surfaces useful for wedging or pushing away bone. In another embodiment, the probe and sheath are integrated into a single piece construction. In use, the cannula may be pre-loaded onto the probe so that the handle of the probe need not be removed to insert the cannula. In one embodiment, illustrated in FIGS. 2A and 2B, the probe body has depth markings. These markings can help the physician determine the position of the cannula as it is being placed in the bone. In addition, the markings may also indicate whether the positioning of the cannula is also moving the probe out of the position selected by the physician.

In one embodiment, the handle is detachable from the long slender body so that the cannula may be placed onto the probe after the probe has been positioned in the bone. The detachable handle may be designed to be disposed of after completion of the surgical procedure. For instance, the handle may be fabricated from low cost polymer material, have a simplified attachment mechanism, or both so that replacement of the disposable handle is relatively inexpensive. In one embodiment, the disposable handle is made from plastic material. One advantage of this embodiment is that the plastic would provide radio-lucent to better view the treated area. Fabrication of the handle may be by machining, molding, or any other method. The handle helps provide a better grip and greater control of the probe during its initial positioning. In addition, the handle also may be used to help remove the probe after the cannula is positioned.

Other items described herein also may be designed to be disposable after use. For instance, the handle for the cannula may likewise be made of low-cost polymer material using any suitable fabrication method. Moreover, many of the tools described herein may be designed with a limited or single use in mind. In one embodiment, for instance, the many of the tools in a kit for performing vertebroplasty may be disposed of after completion of the surgical procedure. In a preferred embodiment, the cavity creating tamp is reusable while the other tools in a kit provided to the surgeon are disposable.

The probe guides the cannula, while the cannula enlarges the hole in the bone and is firmly anchored in this hole. Once the cannula is in its desired position, the probe may be removed by withdrawing it out of the end of the cannula not engaged with the bone.

The Cannula:

The cannula is a guiding tube that, in an embodiment, has a cutting edge on the distal end thereof. The cannula is essentially a long cylindrical tube which guides and holds the tamp in place while the tamp is being used to form the cavity. The cannula preferably has a handle to facilitate rotation and working of the cannula into the bone. More preferably, the cannula has a handle with a hole extending there through that is in alignment with and continuous with the hole extending through body. In one embodiment, the cannula handle is detachable. As described above for the probe handle, the detachable handle may be designed to be disposed of after completion of the surgical procedure. The handle of this embodiment may be fabricated from low cost polymer material so that replacement of the disposable handle is relatively inexpensive. Suitable materials and manufacturing methods for the handle of this embodiment are similar to those described above.

The cannula body preferably is tubular with the hole extending the entire length of the tube. The hole is advantageously, but not necessarily, circular. The hole is configured and adapted so that other tools, such as those described herein, may be inserted into the bone through the cannula hole. It is further preferred that the hole in the cannula allows the bone tamp to be freely rotatable. In an alternative embodiment, either the cannula, the tamp, or both, may be designed to impose a limited range of rotation. For instance, the cannula or probe may have stops that allow the tamp to be rotated within a certain range, but no further. In one embodiment, the limited range of rotation may be adjustable so that the range of rotation may be selected by the physician either before or during the surgical procedure.

In a preferred embodiment, the interior wall of the cannula defines an open cylinder having an inner diameter between about 3 mm and about 7 mm, more preferably between about 3 mm and about 6 mm, and most preferably between about 4.2 mm and about 5 mm. In one embodiment, the exterior wall of the cannula defines a cylinder that is between about 5 mm and about 9 mm. In a more preferred embodiment, the outer diameter of the cannula is between about 6 mm and about 8 mm, most preferably between about 6 mm and about 7 mm. In yet another embodiment, the exterior wall of the cannula defines a cylinder that is between about 4 mm to about 9 mm, more preferably between about 5 mm and about 6 mm, and most preferably about 5.4 mm.

The cannula may be made of a metal, for example a surgical steel alloy, an elastomer, or any other material suitable for surgical devices. The cannula can be constructed, for example, using standard flexible, medical grade plastic materials, like vinyl, nylon, polyethylenes, ionomers, polyurethane, and polyethylene tetraphthalate (PET). The cannula can also include more rigid materials to impart greater stiffness and thereby aid in its manipulation and torque transmission capabilities. More rigid materials that can be used for this purpose include stainless steel, nickel-titanium alloys (NITINOL™ material), and other metal alloys.

In a preferred embodiment, the distal end of the cannula is adapted to cut through skin, tissue, and bone. In one embodiment, for example, the distal end of the cannula has a serrated edge. The end is advantageously circular to ease cutting into the bone. In addition, the cannula may also have a widely spaced thread disposed on the exterior body that assists in inserting the cannula into the bone. The thread may have a low-profile and a steep pitch for relatively quick advancement into and out of the bone. Thus, rotation of the cannula causes the threads to help advance the cannula into the bone. The threads also may be help anchor the cannula into the bone or facilitate removal of the cannula when desired. In one embodiment, the inside of the cannula and the probe may be threaded. This embodiment would provide for a more controlled advancement of the cannula with respect to the probe. Other tools, such as the bone tamps and cannula tamps described herein, also may be threaded so that their deployment inside the bone is more controlled. In an embodiment where the bone tamp is threaded, it is preferred that the pitch of the threads is relatively low so that the bone tamp does not significantly move in the axial direction while the bone tamp is being rotated to create a cavity in the bone.

The Tamp:

The tamp, or curette, is sized and adapted to pass through the cannula and into the cancellous portion of the bone. In one embodiment, where the tamping mechanism is then carefully expanded and rotated to form the cavity. The tamp has a body which is approximately advantageously, but not necessarily, a long cylinder. In one embodiment the an outer diameter or widest portion of the long body is between about 3 mm and about 7 mm, preferably between about 4 mm and about 6 mm, and more preferably between about 4 mm and about 4.5 mm at the point where the body enters the bone. In one embodiment, the diameter or dimensions of the long body is essentially unchanging along the length of the body. The body may be solid or hollow. In many embodiments, there is a groove along one side of the body, wherein a wire or a rod may pass. This wire or rod may be used to control the deployment of the tamping mechanism.

In a preferred embodiment, the tamping mechanism is sized to create cavities wherein the largest radial dimension of the flapper, or tip, measured from the axis of the body is between about 4 mm and about 24 mm, preferably between about 6 mm and about 20 mm, more preferably between 8 mm and 16 mm, and even more preferably between about 10 mm and 12 mm. Several tamping mechanisms having tips of varying lengths also may by provided so that the physician can determine the size of the cavity to create during the surgical procedure. In one embodiment, four tamps are provided with tip lengths of about 4 mm, about 6 mm, about 8 mm, about 10 mm, and about 12 mm. Other combinations of tamps having varying tip lengths also may be selected according to the desired sweep of the of the tamps.

This body and the tamping mechanism may be made of metal, for example a surgical steel alloy, an elastomer, or any other material suitable for surgical devices. The body and/or the tamping mechanism can be constructed, for example, using standard flexible, medical grade plastic materials, like vinyl, nylon, polyethylenes, ionomers, polyurethane, and polyethylene tetraphthalate (PET). The body can also include more rigid materials to impart greater stiffness and thereby aid in its manipulation and torque transmission capabilities. More rigid materials that can be used for this purpose include stainless steel, nickel-titanium alloys (NITINOL™), and other metal alloys.

The body typically has the appearance of a long rod or tube. The tamp is designed to have its distal end pass through a cannula and through a passageway cut into the bone. The tamping mechanism, which is on the distal end of the body, therefore also passes through the cannula and into the bone. The other end of the tamp body is controlled by the physician.

The body advantageously may have markings along its length so that the physician may quickly and easily determine the depth at which the tamp reaches into the bone. Preferably, the depth markings correspond to the length from the marking to the tip of the tamp when it is not deployed. That is, the markings indicate the distance to the tip before it is deployed. The physician is able to freely slide the tamp axially within the guide cannula to deploy it in the targeted treatment area. Alternatively, adjustable stops may be provided on the cannula, the tamp, or both in order to control the axial travel of the tamp or its range of rotation. The use of stops in this manner helps the physician to predetermine the size, length, and location of the cavity created. In addition, the adjustable stops also may allow the physician to gradually create the cavity within controlled parameters.

The physician-controlled end of the body contains a handle and a controlling mechanism by which the tamping mechanism may be deployed during tamping and retracted or un-deployed for removal of the tamp from the bone. While a motor may be used to effect rotation, it may be preferable in certain uses to manually rotate the tamp so that, for example, the physician may feel how easily the tamp is rotated. Manual operation of the tamp may provide a more tactile sense of the anatomy in and near the created cavity. In addition, manual operation of the tamp also may provide a sense of the degree to which the cavity has been completely created. If manual rotation of the tamp is resisted, for instance, the desired cavity size may not yet be created.

The tamp handle may be removable, but during manual operation of the tamp this handle should be fixed to the body. This handle is preferably sized and shaped to facilitate easy handling and rotation—that is, sized and shaped like a screwdriver handle. The handle also may be configured to indicate to the physician which direction the flapper is pointing. For example, the handle may have a flat surface on it in the direction where the flapper extends. Alternatively, the handle may have a texture, indentation, or other marking indicating the position of the flapper.

The handle also may be shaped like a pistol grip, where squeezing the grip effects a rotation of the tamp tip to its extended position. There may be a locking nut to hold the body of the tamp to the handle. Once the top is locked in position by the locking nut, the grip may be rotated to create the cavity in the bone. In addition, the locking nut may be configured so that the pistol grip may be partially squeezed and then locked in place so that the flapper is held in a position that is not fully extended. Other locking mechanisms may be used instead of a locking nut. In one embodiment, a ratchet mechanism is used to prevent the pistol grip from opening until the ratchet is released. The ratchet can have audible clicks that indicate to the physician the degree to which the flapper has been extended.

In one embodiment, the locking mechanism has markers that indicate to the physician the amount of sweep a flapper tip will provide when it is partially or fully deployed. Thus, a marker may indicate to a physician that the sweep of the flapper tip as it is rotated is only half the sweep of the flapper tip when it is fully extended. These markers may be provided on any portion of the tool. In one embodiment, the markers indicate the percentage of sweep that is achieved with respect to a fully extended tip. For example, the physician may select a setting for the flapper tip to provide only 50% of the sweep based on the marker indications. In another embodiment, the markers indicate the actual amount of sweep. In this embodiment, a physician may select the size of the cavity to be created by the marker indications. In yet another embodiment, the markers indicate the angle at which the flapper tip is deployed. Any or all of these embodiments may be used in combination with each other.

The tamp controlling mechanism controls the deployment of the tamping mechanism on the distal end of the body. Therefore, most embodiments of the tamp provide a control mechanism which runs alongside, or within, the tamp body. The controlling mechanism may move a rod, or extend a wire, or the like, wherein the rod or wire controls the degree to which the tamping mechanism is or may be deployed. In some embodiments, the controlling mechanism provides precise positioning of the tamp. In other embodiments, the controlling mechanism limits the range of motion in which the tamp may move, preferably gradually limiting the range of motion until the tamp is securely held in a single position.

Any method or device may be used to control the deployment of the tamping mechanism. In one embodiment, the controlling mechanism is a thread and a threaded collar, whereby rotating the collar relative to the handle of the tamp causes the tamping mechanism to expand, contract, or otherwise be deployed, such as by advancing or retracting the sheath around the tamping mechanism, advancing a rod or similar device to limit the range of motion of the tamp, or the like. Alternatively, the controlling mechanism may limit the expansion or contraction of the tamping mechanism.

Preferably, the thread has interruptions, such as flat sides cut at regular intervals, which interact with a locking pin and/or a bearing located within the collar. The locking pin or bearing, when in alignment with the interruptions of the threaded body, moves into the interruption to at least partially resist further turning of the collar. Preferably, the interruptions provide an audible and tactile click. As the collar is rotated further, the locking pin or bearing moves out of the interruption.

In an alternative embodiment, the thread does not have interruptions that provide an audible and tactile click. In this embodiment, the thread and collar have a continuous range of motion due to the absence of a locking pin or bearing moving in and out of thread interruptions as described above. In this embodiment, it is preferred that a locking or braking device can be applied to provide some resistance to rotation of the collar. The locking or braking device also may be designed to hold the collar in the position desired by the physician so that the collar does not slip or rotate out of position during use of the bone tamp to create a cavity.

In practice the controlling mechanism may in fact move the body of the tamp, relative to the handle such that the rod or wire, which may be fixed to the handle, appears to advance or retract when viewed at the distal end of the body. Alternatively, the controlling mechanism may cause the tamp to expand, contract, or otherwise be deployed by moving the tamp itself. In either example, the collar may be fixed to the handle in a manner that allows for rotation of the collar about the handle while restricting the collar from moving along the longitudinal axis of the handle.

In one embodiment, the tamp uses a directional tip, i.e., a flapper, attached to the distal end of the tamp as the tamping mechanism. The flapper may be hinged on one end to allow movement of the flapper relative to the body in one plane. In this embodiment, the flapper is hinged, and connected thereby, to the distal end of the cylindrical body so that the distal end of the flapper can be displaced out of alignment with the body so that when the flapper is rotated out of alignment with the body it provides a greater effective radius at the distal end of the tamp. Thus, when the tamp is rotated the flapper can displace cancellous tissue away from the tamp.

In a preferred embodiment, the flapper is hinged, and connected thereby, to the distal end of the tamp body so that the distal end of the flapper can displace itself out of alignment with the body to its maximum extent, and wherein the control rod when extended limits the effective radius at the distal end of the tamp.

In one embodiment, the flapper may move about the hinge, when unimpeded by the cannula or by the controlling mechanism, through an arc ranging from 0 degrees to between about 60 degrees and about 150 degrees, preferably to between about 80 degrees and about 120 degrees, and most preferably to about 90 degrees, with an angle of 0 denoting alignment with the tamp body. In a preferred embodiment, the range of motion of the flapper can be gradually limited by the control mechanism. For example, as the physician turns the collar as described above, the range of motion of the flapper is restricted from returning to alignment with the tamp until eventually the control mechanism securely holds the flapper in a single position. As mentioned above, it is most preferred that the final position of the flipper is about 90 degrees, although a final position in the ranges noted above may also be suitable.

In another embodiment, deployment of the flapper is controlled such that the flapper has little, if any, range of motion when the flapper is in any position. Thus, in this embodiment, partially turning the collar of the tamp results in partially extending the flapper out of alignment with the tamp body with little, if any, range of motion available to the flapper in any given position. This embodiment provides an advantage of allowing the physician to partially extend the flapper to create a cavity of a smaller diameter than when the flapper is fully extended. When the flapper is to be partially extended in order to gradually create the cavity, it is preferred that a locking or braking device as described above is used to help prevent the flapper from moving out of its desired position.

While the flapper may be configured and adapted to cut the cancellous tissue, compact or tamp it, or both, in one preferred embodiment the flapper has a blunt tip that primarily compacts the tissue. The blunt tip also may be used to effect reduction of a fracture. In vertebroplasty, for example, the physician may use the blunt tip to perforate the front surface of the vertebrae in order to effect a reduction. In addition, the physician may use the tip to move or reposition the endplate or other bony fragment to help restore the bone to its natural anatomy.

The flapper also may be curved or may have curved edges to further promote tamping back cancellous tissue when the tamp is rotated. In some applications, cutting may be preferred over tamping. Thus, the flapper may be configured and adapted to suit the particular application or desired result, such as by using a more aggressive flapper shape to cut tissue instead of tamp it. For instance, in one embodiment the edges of the flapper are designed to cut cancellous material when the flapper is rotated. A preferred flapper is a curved cup-type shape. The flapper may also be a cylindrical rod shape, or a flattened cylindrical or oval shape, a curved propeller-type shape, or a paddle shape. This flapper tip also may be rounded to minimize cutting.

In one embodiment of the tamp with a flapper having a gradually limited range of motion as described above, there is a rod which passes up a groove in the side of the tamp or, alternatively, up a groove inside the body of the tamp. In this embodiment, the rod is part of the controlling mechanism which, when in its retracted mode, does not interfere with the movement of the flapper. In its fully extended mode, the rod impinges on the flapper on one side of the hinge, which causes the flapper to be displaced from its alignment with the tamp body toward the other side of the hinge to its greatest extent. When the rod is in an intermediate position, the flapper can move from a point somewhat displaced from its alignment with the tamp body where the rod is impinging on the flapper to a point of maximum displacement from its alignment with the tamp body. It is preferred that the linkage is a single part to maintain simplicity in design and use.

Another tamp embodiment employs a expandable ring made from memory metal, i.e., a superelastic nickel titanium alloy such as NITINOL™. The expandable ring has a preformed shape so that when the memory metal or NITINOL™ body is retracted into the body of the tamp there is no expanded ring, and as the NITINOL™ body exits from the body of the tamp an expanding ring is formed. The structure comprises a ribbon of resilient inert memory metal, which is bent back upon itself and preformed with resilient memory to form a ring. This expandable ring is the tamping mechanism.

The expandable ring may be formed into any desired shape. It also may be symmetrical about an axis or asymmetrical, depending upon the desired performance of the tamp. Moreover, the expandable ring may be formed such that a portion or side of the ring expands more than another so that the ring appears to be off-center from the longitudinal axis of the tamp body. In one embodiment, the ring is oval in shape, while in another the ring is D-shaped. In other embodiments, the expandable ring forms a polygon, which may have regular or irregular sides and angles.

In a preferred embodiment, the memory metal is in the form of a flattened ribbon. In another preferred embodiment, the edges of the expanding memory metal ring are blunted and/or curved to minimize cutting and to maximize displacement of the cancellous tissue during rotation. Manipulation of the ribbon, i.e., expanding and contracting as well as rotating, when inside bone tamps creates a cavity in the cancellous bone.

In one preferred embodiment, called the symmetrical ring embodiment, the expandable ring when in its fully expanded position forms a ring-like structure with a point on the distal end of the body. In a variation of this embodiment, the ring forms a hexagonal-type structure with one point on the distal portion of the ring and a second point near the body of the tamp. In another embodiment, the ring when in its fully expanded position forms a circular or oval structure, or flattened version thereof. In a third embodiment, the ring forms a rounded triangle, where the radius of each corner of the triangle is beneficially at least 3 mm. In these embodiments, the deployment of the ring can be affected by either a wire which allows deployment and retraction of the ribbon outside the body of the tamp, wherein feeding wire in expands the ring and pulling wire out retracts the tube, or in the case of preformed tubes by pushing the tube outside the body, for example with a rod, wherein as more of the ribbon extends past the body of the tube, the ring or other structure will grow or expand in size or length. The option of feeding and retracting wire is preferred.

In a particularly preferred embodiment, the ring forms an asymmetrical ring. In practice, this ring may form a shape of a "D". In this embodiment, one end of the ribbon forming the ring may be attached to a rod while the other end runs back towards the handle. The controlling mechanism in this embodiment controls the expansion of the loop. Of course, the "D" shape of the asymmetric loop is pre-formed. In its fully withdrawn position, the ring is sufficiently compact to fit into the tamp body.

The cannula, tamping body, and/or tamping mechanism may have disposed thereon one or more radiological markers. The markers are made from known radiopaque materials, like platinum, gold, calcium, tantalum, and other heavy metals. The markers permit radiologic visualization of the loop structure, tamp body, and/or cannula within the targeted treatment area.

The systems and methods embodying the invention can be adapted for use virtually in any interior body region, where the formation of a cavity within tissue is required for a therapeutic or diagnostic purpose. The preferred embodiments show the invention in association with systems and methods used to treat bones. The systems and methods which embody the invention are well suited for use in this environment. It should be appreciated that the systems and methods which embody features of the invention can be used in most bone structure, including but not limited to the vertebra.

The invention also provides directions for using a selected tool according to a method comprising the steps of deploying the tool inside bone and manipulating the structure to cut cancellous bone and form the cavity. The method for use can also instruct filling the cavity with a material, such as, e.g., bone cement, autograft material, allograft material, synthetic bone substitute, a medication, or a flowable material that sets to a hardened condition.

The cavity may be irrigated and/or aspirated to clear the cavity prior to delivery of bone filler material. In addition, inflatable devices, such as a surgical balloon or similar device, may be used when treating the bone. These methods and devices are further described in pending U.S. application Ser. No. 09/908,899, entitled "Inflatable Device and Method for Reducing Fractures in Bone", which is incorporated by reference herein in its entirety.

BRIEF DESCRIPTION OF THE DRAWINGS

FIGS. 4A–C are three views, two of which are side and end views of a probe handle (FIGS. 4A and 4B), and one of which is a partial view of one end of a probe body that connects to the probe handle (FIG. 4C).

FIGS. 5A and 5B illustrate side and end views of cannula handles.

FIG. 8A is a view of an exemplary embodiment of a cleaning, or flushing, bar.

FIG. 8B is a view of another embodiment of a cleaning, or flushing bar.

FIGS. 9A and 9B are two views, 90 degrees apart in perspective, of a bone tamp of the memory metal ring embodiment.

FIGS. 10A–C are three views of a memory metal ring at different levels of deployment.

FIGS. 15A–C are views of a bone tamp of the rod and memory metal filament for use with the asymmetric memory metal ring embodiment.

FIGS. 18A–E are five views of details of the flapper and hinge.

DETAILED DESCRIPTION OF PREFERRED EMBODIMENTS

The present invention is directed to tools and methods for creating cavities in bone. The creation of cavities in bone may be beneficial when bone filler material is to be introduced to the interior of the bone. One advantage is that the creation of a cavity may be used to restrict, contain, or control the delivery of the bone filler material. Another advantage is that the cavity enables the flow and placement of filler material to a desired region.

A combination of the tools described herein may be provided to a physician as a cavity creation system. In one embodiment, the combination of tools are provided in kits according to stages of the procedure in which the tools will be used. For instance, one combination of tools may be selected for a cavity creation approach kit. The cavity creation kit may include, for example, probes, cannulas, and displacement rods. These tools, which are described in greater detail below, can be used to provide access to the treated area.

Another combination of tools can be selected to create a cavity creation instrument set. The cavity creation instrument set may include, for example, a combination of bone tamps (or curettes). Once access to the treated area is obtained, the tools in the cavity creation instrument set may be manipulated to create cavities in bone. In one embodiment, these two kits provide all of the tools for the cavity creation system. In another embodiment, other tools, materials, or kits may be added according to the particular procedure the physician may want to perform. Preferably, and as described below, the cavity creation approach kit is a combination of tools that can be disposed of after use, while the cavity creation instrument set is made of tools that can be used again in future procedures.

The description that follows refers to the drawings listed above.

Figure 1A:
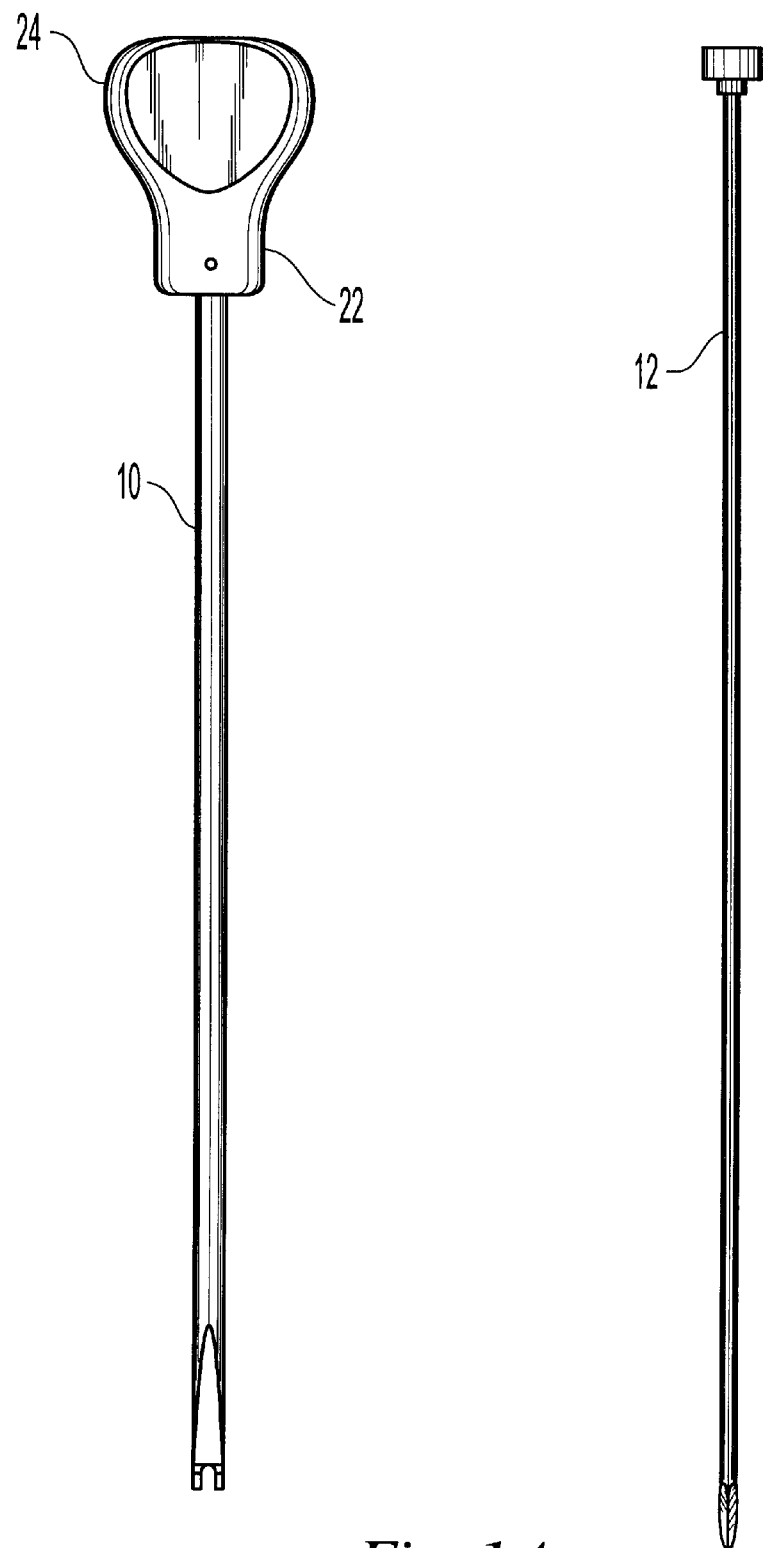
FIG. 1A is a view of a assembled probe body and handle and of a probe tip.
Figure 1B:
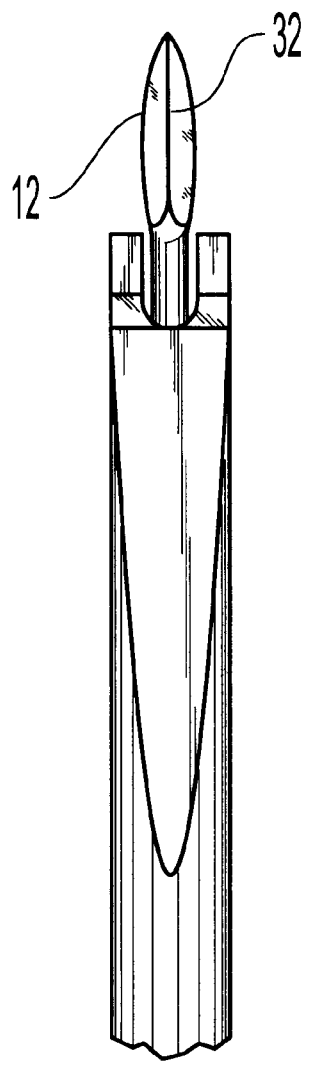
FIG. 1B is a view of a the distal end of an operational probe.

The Probe:

FIGS. 1A and 1B illustrate one embodiment of a probe tip of the present invention.

Figures 2A, 2B, 2C:
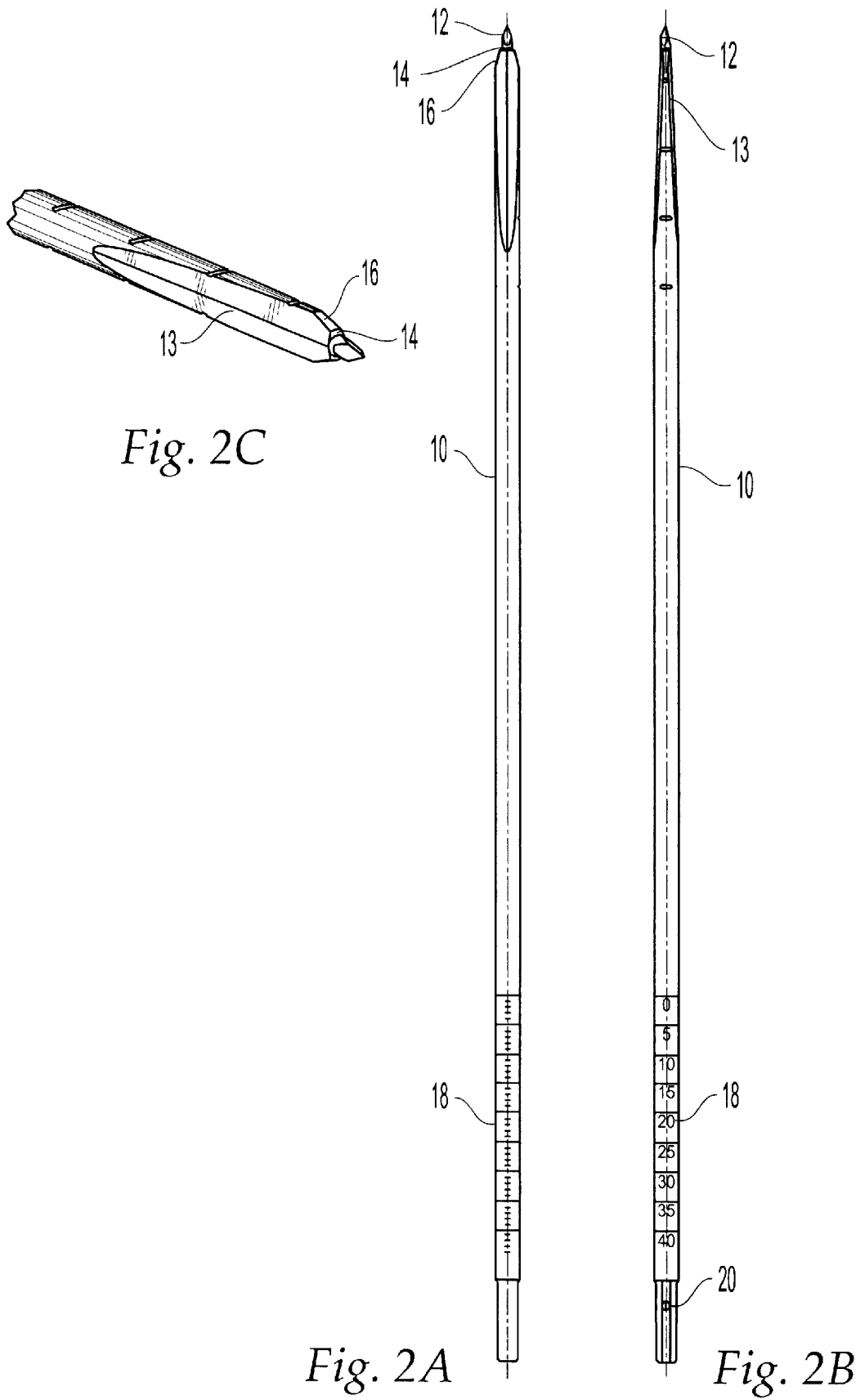
FIGS. 2A–C are two views, 90 degrees apart in perspective, of a probe body (FIGS. 2A and 2B), and a view of the probe tip from a forward perspective (FIG. 2C).

The probe sleeve 10 is adapted to have the probe tip 12 fit slidingly therein. As seen in FIG. 1B, the distal end of the probe tip 12 extends past the distal end of the probe sleeve 10. In one embodiment, the distance that the tip extends beyond the sleeve may be predetermined. In addition, this distance may be selectively varied according to the physician. If the distance between the tip and the sleeve is predetermined but not selectable, it is preferred that the probe sleeve and probe tip be constructed as a single piece, as shown in FIGS. 2A–C. FIGS. 2A and 2B are side-view drawings of a probe sleeve 10, and FIG. 2C is a forward perspective looking only at the distal end.

The distal end of the probe tip and probe sleeve may be shaped to help the probe enter the cortical region of the treated bone. In one embodiment, the probe tip grips the cortical bone but does not pass completely through it. In another embodiment, the probe tip and sleeve are worked into the cortical bone and into the cancellous region inside. Thus, the distal ends of the probe tip and probe sleeve may be designed according to their desired functionality.

In one embodiment, the distal end of the probe sleeve 10 is beveled. The sleeve 10 extends from the probe tip for a distance ranging from about 0.05 to about 0.5 millimeters, say about 0.1 to 0.2 millimeters, at a sharp angle, for example between about 30 degrees and about 90 degrees, preferably between about 45 degrees and about 75 degrees, more preferably between about 55 and about 65 degrees, wherein the angle is measured from an imaginary line running axially with the probe sleeve 10. This provides a strong surface that may face shearing action from bone during insertion. As shown in FIG. 2A, the angle of the bevel is then changed to a more gentle angle, say between about 5 and about 45 degrees, preferably between about 15 and about 35 degrees, and maintains approximately this angle until the outer diameter of the probe sleeve 10 is matched. This provides a gentle surface 16 for displacing bone during insertion. When viewed at another angle, shown in FIG. 2B, the probe sleeve is even more gently angled, with the angle ranging from about 5 to about 30 degrees, providing another gently sloping surface 13 to displace bone. There is a distance scale 18 on the exterior of the probe sleeve 10. Finally, there is a hole or indentation 20 in the sleeve. This hole contains a bearing 22 or set screw 22 which locks the probe tip into the probe sleeve. The hole may be beveled to allow the bearing or screw to move to disassemble the probe.

The probe tip 12 can be seen in its entirety in FIG. 1A, though the groove in which the bearing 22 sits can not be seen. Also shown in FIG. 1A is a probe sleeve 10 and a handle 24 and set screw 22. A close-up of the distal end of the probe sleeve 10 and probe tip 12, after assembly, is shown in FIG. 1B. It can be seen that in this embodiment the probe tip has a point formed by making a diagonal cut 32 through the round probe tip. Other methods and shapes for forming a point are equally acceptable.

Figure 3C:
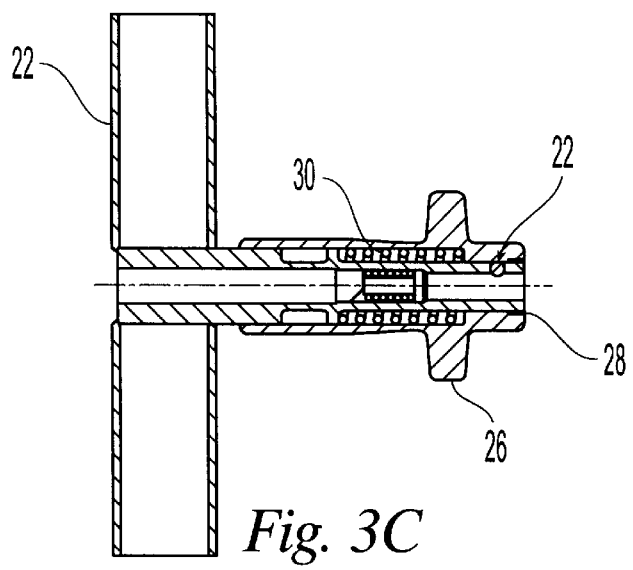
FIGS. 3A–C are three views of a probe handle, one of which is a side view of the handle, and two of which are cross-sectional views that are 90 degrees apart in perspective.
Figure 3B:
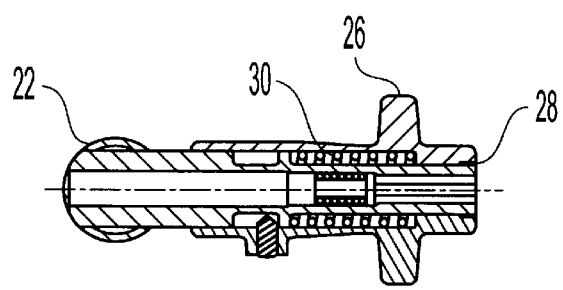
Figure 3A:
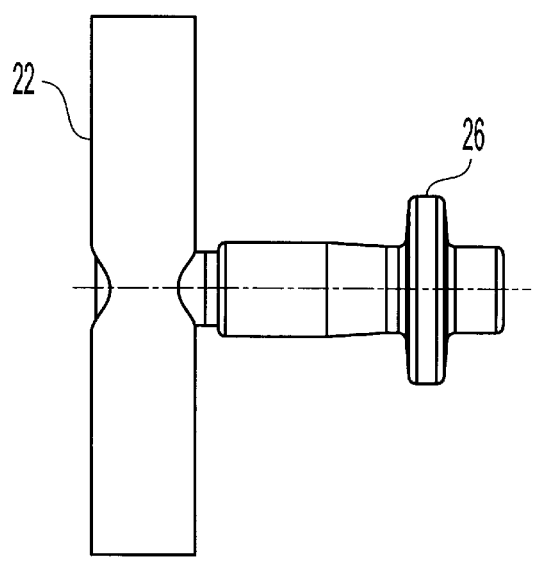

It is preferred that the probe has a handle on its proximal end for the physician to better manipulate and position the probe. FIGS. 3A–C contain several perspective drawings of a handle 24 for the probe. In this embodiment, the handle has a probe collar 26 which, when in its downward position as shown, locks the bearing 22 into place, thereby securing the probe tip 12 (not shown). The probe tip 12 has a groove sized and positioned to accept a portion of the bearing 22, thereby preventing the probe tip 12 from moving axially in the probe sleeve 10. The probe collar 26 has a groove 28 on its interior surface, wherein if the groove 28 is slid to intersect the bearing 22 then the bearing 22 will disengage from the probe tip 12 and the probe tip 12 can be slid axially. A spring 30 provides downward force on the probe collar 26, so to disengage the probe tip 12 the physician must overcome the force of the spring and slide the collar up toward the handle 22.

In another embodiment, illustrated in FIGS. 4A–E, the handle of the probe may be designed so that it may be removed and discarded after its use. Under these circumstances, it is preferred to design and construct the handle such that is can be replaced at a relatively low cost. Thus, it may be desirable to mold the handle from inexpensive materials that are capable of use in conventional manufacturing processes. Commercially available polymers are one example of materials that may be used to lower the replacement cost. For instance, the handle may be made of injection-molded or machined plastic.

Figure 4D:
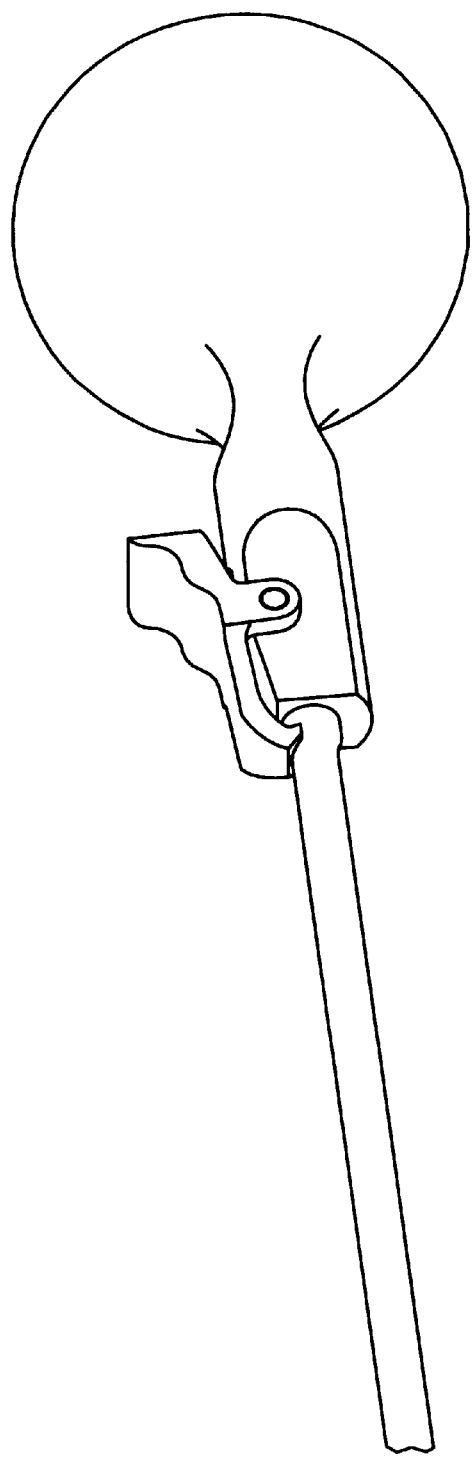
FIG. 4D is perspective view of an exemplary embodiment of a probe handle.
Figure 4E:
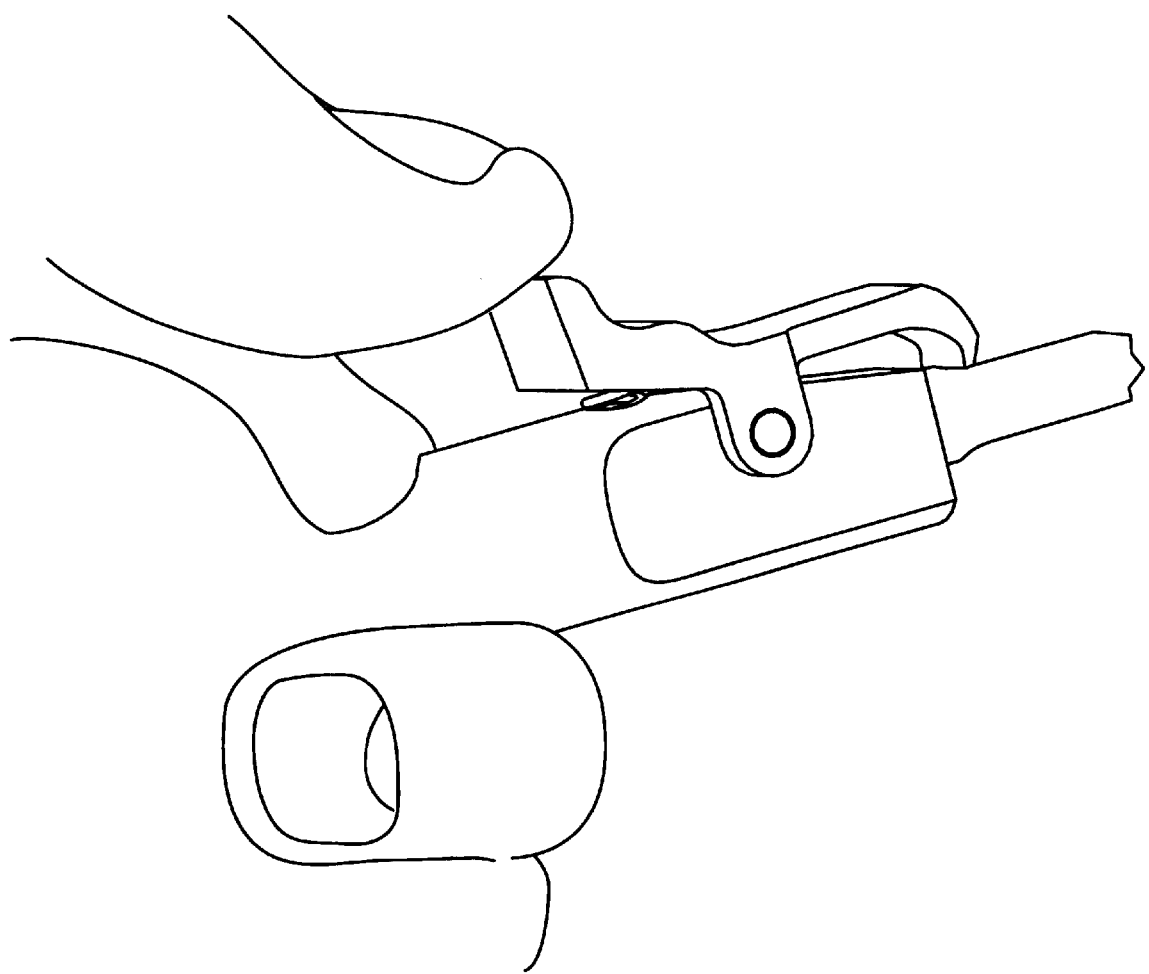
FIG. 4E is a perspective view of a coupling mechanism for releasably securing the handle of FIG. 4D to a probe.

In addition, the mechanism that attaches the handle may be simplified in order to reduce costs. For instance, as shown in FIG. 4E, the handle may be attached to the probe with a spring-loaded latch that has a protrusion that engages with a notch in the probe sleeve. When the latch is depressed, the protrusion disengages from notch so that the handle can be removed. Preferably the protrusion and notch engage in a manner that provide some resistance to torsional forces. In this embodiment, the physician may be able to manipulate the probe by rotating it from time to time to work the probe tip into position.

Figure 5A:
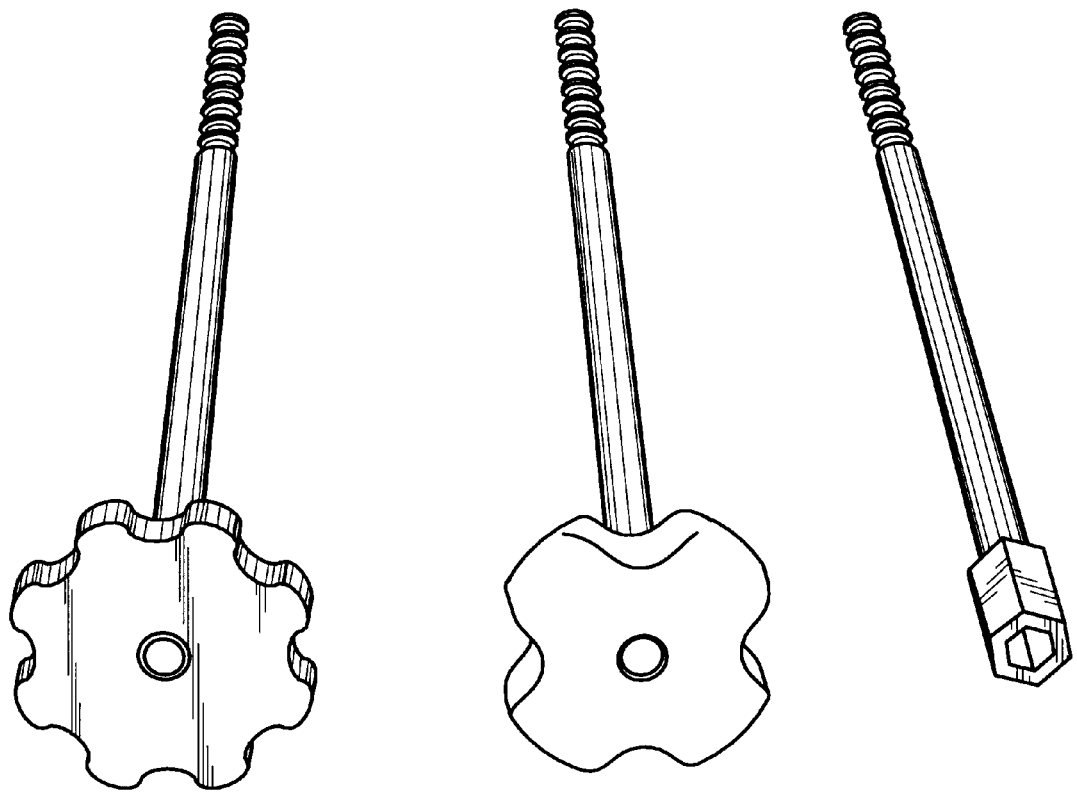

Just as the probe handle may be designed to be removed and discarded after use, handles for other tools described herein also may be removable or designed to be disposable. The cannula, for example, may likewise have a removable handle. In addition, if it is desired to have most of the tool kit be disposable, the handle may be made of inexpensive materials, such as commercially available polymers or plastic as described above. FIGS. 5A and 5B illustrate two cannulas, one having an attached handle and the other a removable handle.

Figure 6:
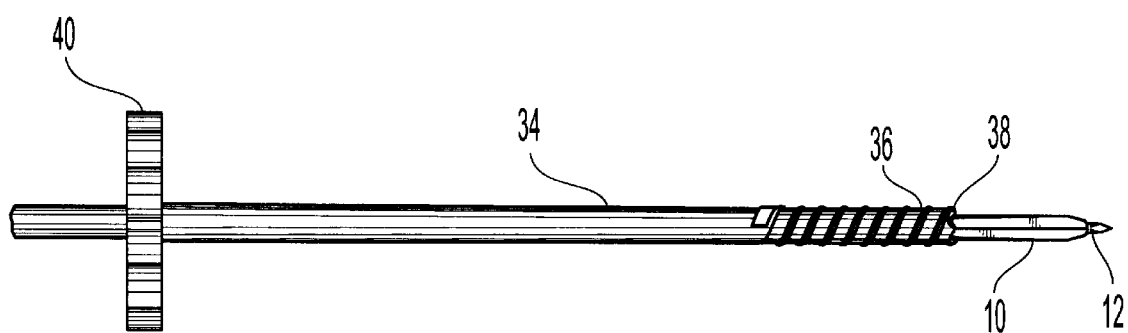
FIG. 6 is a view of a probe extending through a cannula.

The Cannula:

Once the probe is in position, the probe handle may be removed and so that the cannula can be slideably placed over the probe sleeve. If the probe handle is not removable, the cannula may be slid onto the probe prior to positioning the probe into the bone. FIG. 6 shows the probe assembly of FIGS. 1A and 1B passing through a cannula 34. The cannula 34 has optional threads 36, a cutting edge 38, and a handle 40.

Figure 7B:
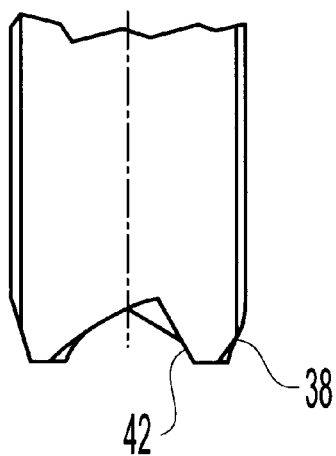
FIGS. 7A–D are views of cannulas and distal ends of cannulas.
Figure 7A:
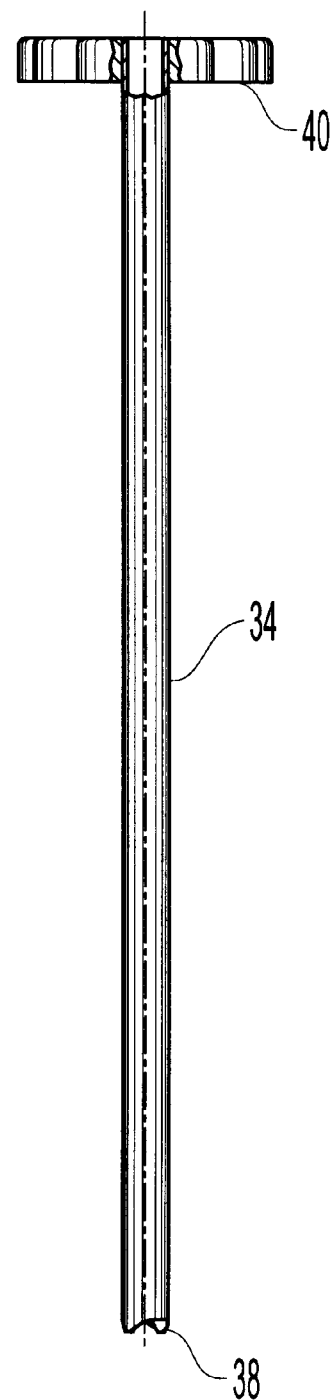
Figure 7C:

The cannula 34 is more clearly shown in the drawings of FIGS. 7A–D. Details of the cutting edge 38 show that there are cutting surfaces 42, preferably set at an angle of 30 degrees, though the angle could range from 20 degrees to about 80 degrees. Preferably the angle of the cutting edge is between about 30 degrees and about 50 degrees. In the embodiment shown in FIG. 7B, the edges have a pitch of about 7.5 millimeters on a 5.4 millimeter outer diameter cannula. As shown in FIG. 7C, the cutting edge of the cannula may have a less aggressive cutting surface, such as a circular terminating edge. The terminating edge may be beveled to provide a sharper cutting surface. Alternatively, the terminating edge may be rounded or blunt or have another profile that provides certain performance characteristics or a particular feel. These illustrative variations may be selected, among other shapes, according to the desired feel or performance of the cannula.

The threads 36, when present, are beneficially raised between about 0.05 mm and about 0.5 mm, and more preferably between about 0.2 mm to about 0.3 mm, above the body of the cannula body 34. The cannula body 34 can have an outer diameter of between about 3 mm and about 7 mm, preferably between about 4 mm and 6 mm, more preferably between about 5 mm and 5.5 mm. In one embodiment, the cannula 34 is a tube, where the wall of the tube is between about 0.2 mm and about 1 mm, preferably between about 0.3 mm and about 0.6 mm, in thickness.

Figure 7D:
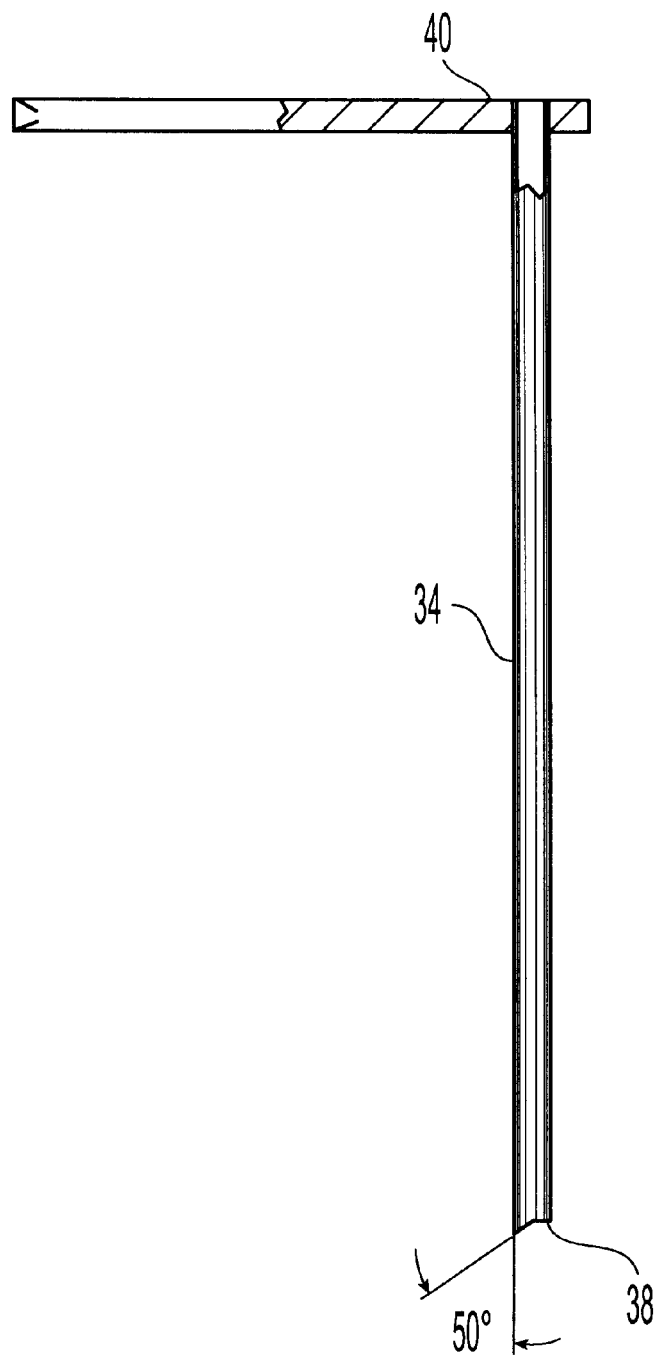

FIG. 7D shows a cannula 34 without threads. In this cannula, the handle 40 is a bar handle as opposed to a circular handles of the cannula of FIG. 5A. The bar handle may be preferred in some instances because there may need to be a significant amount of torque put on the cannula while edging or cutting the cannula into the bone. These different handle designs may be used interchangeably with any cannula design. For instance, the cannula body 34 shown in FIG. 7 has an outer diameter of about 4.8 millimeters. The angle of the cutting surfaces 42 is about 50 degrees.

Figure 8C:
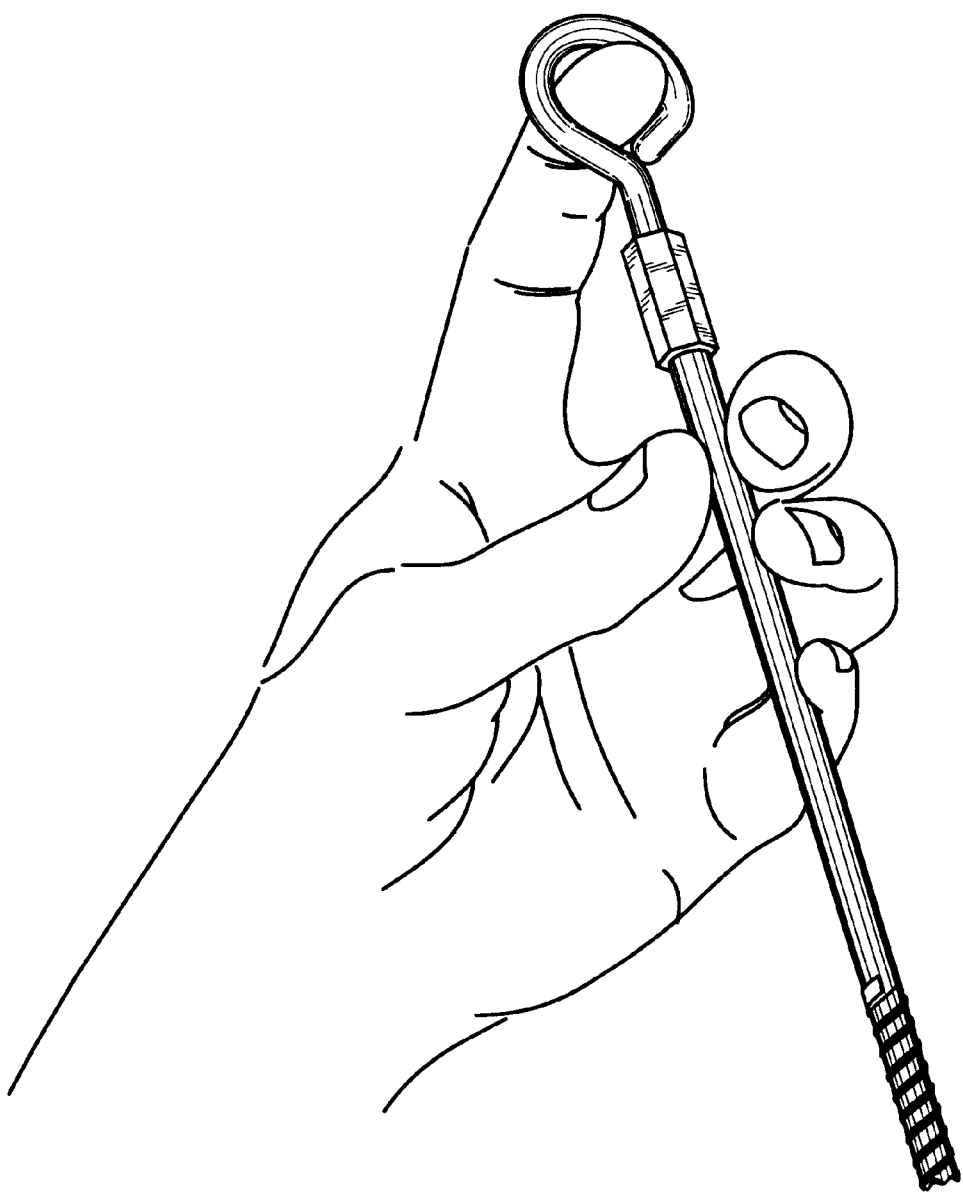
FIG. 8C is a view of the cleaning, or flushing bar of FIG. 8B slidably received in a cannula.
Figure 11C:
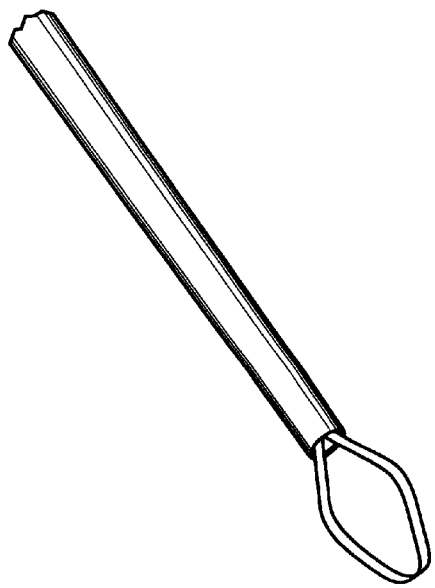
FIGS. 11A–D are four views of a memory metal ring at different levels of deployment.
Figure 11A:
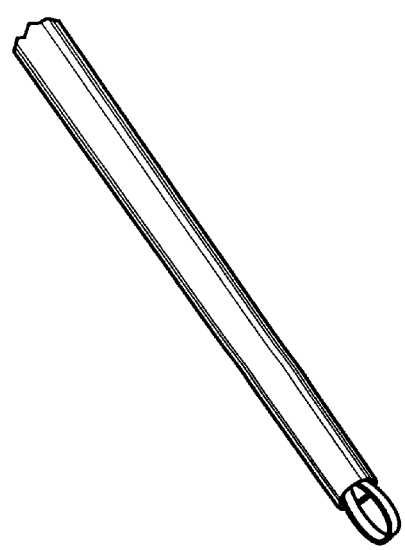
Figure 11D:
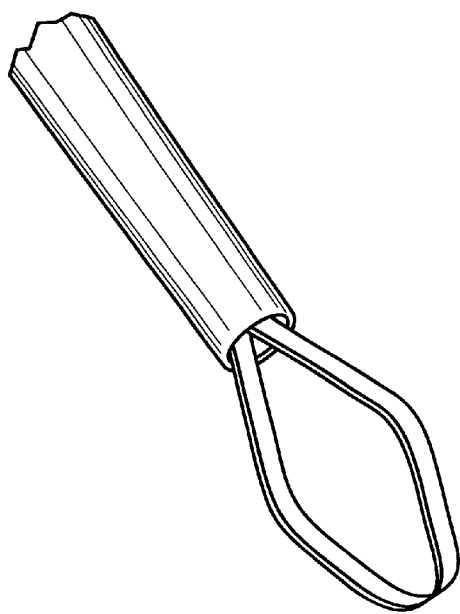
Figure 11B:
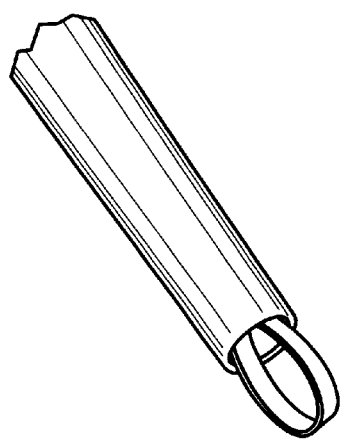

Displacement Rods:

FIGS. 8A and 8B show displacement rods for the cannula where the tolerance between the displacement rods and the cannula is between about 0.1 mm and about 0.5 mm. These displacement rods are used to remove debris from the cannula, as illustrated in FIG. 8C. In addition, the displacement rod can be used to push bone filler material into the cavity. In this embodiment, bone filler material can be placed directly into the cannula and subsequently pushed into the cavity.

The tip of the displacement rod that is placed within the cannula may be of any suitable shape for clearing the passage of debris or for introducing bone filler into the cavity. For instance, the tip shown in FIG. 8A has a blunt end, while the tip shown in FIG. 8B has a rounded end. The rounded end may help the physician introduce the displacement rod into the cannula. One skilled in the art would appreciate that other shapes, such as a concave surface, a tapered end or a beveled side, may also be used.

Preferably, the displacement rod is designed to be a disposable tool when it is part of the cavity creation approach kit. FIG. 8B shows one design that may be used to lower manufacturing and replacement costs. The displacement rod in this embodiment is made of a single piece of material. The handle is a ring that is configured to allow the physician to manipulate the displacement rod while in use, as illustrated in FIG. 8C.

Displacement rods also may be used to clear other tools used in the procedure as well. For instance, if a syringe is used to insert bone filler material into the cavity, similar displacement rods also may be used to clear the needle of the syringe. The tolerances between the outer surface of the displacement rod and the inner surface of the area to be cleared may be selected according to the degree that the passageway should be cleared and the relative ease of use of the tool. Small tolerances between the surfaces, for instance, may better clear the passageway but also be more time-consuming or difficult for the physician.

Additionally, tools similar in construction to displacement rods may be used to create a channel inside the cancellous region of the bone where the bone tamp may be used. For instance, once the cannula has been properly positioned to provide access to the interior of the bone, it may be desirable to insert a rod-like tool inside the cannula and into the bone that will clear, or at least loosen, the cancellous bone where the bone tamp will be inserted. This may make insertion of the bone tamp into its desired position easier for the physician. In addition, clearing or loosening the cancellous bone in the area where the tamp will be inserted also may help extend the useful life of the bone tamp since it will not be subjected to forces on the distal end in order to push through the cancellous bone.

Bone Tamps:

Once the cavity creation approach has been established using any or all of the tools and methods described above, bone tamps, or curettes, are used to create a cavity inside the bone. The bone tamps, described below in greater detail, may be made in a variety of ways according to the particular performance or feel sought by the physician. Thus, in one embodiment the bone tamp is made with shape memory metal, another uses a flapper that turns through a range of motion, and yet another uses a flapper that has a controlled range of motion. The embodiments described below are non-limiting examples of the present invention.

FIGS. 9A and 9B show two views of a memory metal expanding ring bone tamp. The body 44 is shown to be substantially cylindrical, but the cross section may be of almost any type. The body 44 in this embodiment is about 4.2 plus or minus about 0.2 millimeters in outer diameter. The size of the body is not important so long as the body 44 and the ring 46, when retracted, pass through the interior diameter of the cannula. There is a distance scale 48 set in millimeter increments. The length of the body 44 is about 190 millimeters, but this length can vary. The memory metal loop 46 is shown in the expanded position where it has a diameter of about 10 millimeters and a length of about 15 millimeters. The range of expansion for an expanding ring tamp is beneficially between about 4 to about 24 millimeters, preferably between about 6 and about 20 millimeters, more preferably between about 8 and about 16 millimeters.

In this embodiment the collar 50 has a bearing/set screw 52 that slides in channel 54. The mechanism by which the collar is advanced or retracted includes but is not limited to sliding, turning a threaded collar, or even squeezing a pistol grip. Channel 54 is firmly anchored to handle 56. Therefore, when the collar 50 with its bearing or set screw 52 slides in channel 54, the collar 50 and body 44 moves relative to the handle 56. By sliding the collar toward the ring 46, the ring 46 is retracted into the body. The controlling mechanism for the memory metal loop involves withdrawing the memory metal loop 46 into the body 44. In its fully withdrawn state, the memory metal loop 14 shall not exceed past the body 10 by more than about 4 millimeters, preferably by no more than about 2.5 millimeters. The ring 46 is firmly fixed to the handle 56. The push button 58, under a force exerted by spring 60, and tapered bushing 62, keep the rod or wire 64 which is continuous with the memory metal ring 46 firmly fixed to the handle 56. Depressing the push button 58 allows the rod to slide, loosening the gripping force between the rod and the handle. This push button is used when disassembling the tamp for cleaning. Note that a set screw 66 can be used to lock the push button to prevent accidentally releasing the ring assembly.

The physician can expand the memory metal loop 46 by pulling back the collar 50. There is advantageously in collar 50 a thumb hold to give good control over this slidable collar. The collar is held in place by friction, the thumb-force, and optionally with a set screw. The channel 54 has a discrete beginning and end, therefore limiting the amount the body 44 can be slid relative to the handle 56. The channel 54 may have side-facing depressions or grooves which with a twist allow the collar to be "locked" in one of several pre-selected positions.

Figure 12:
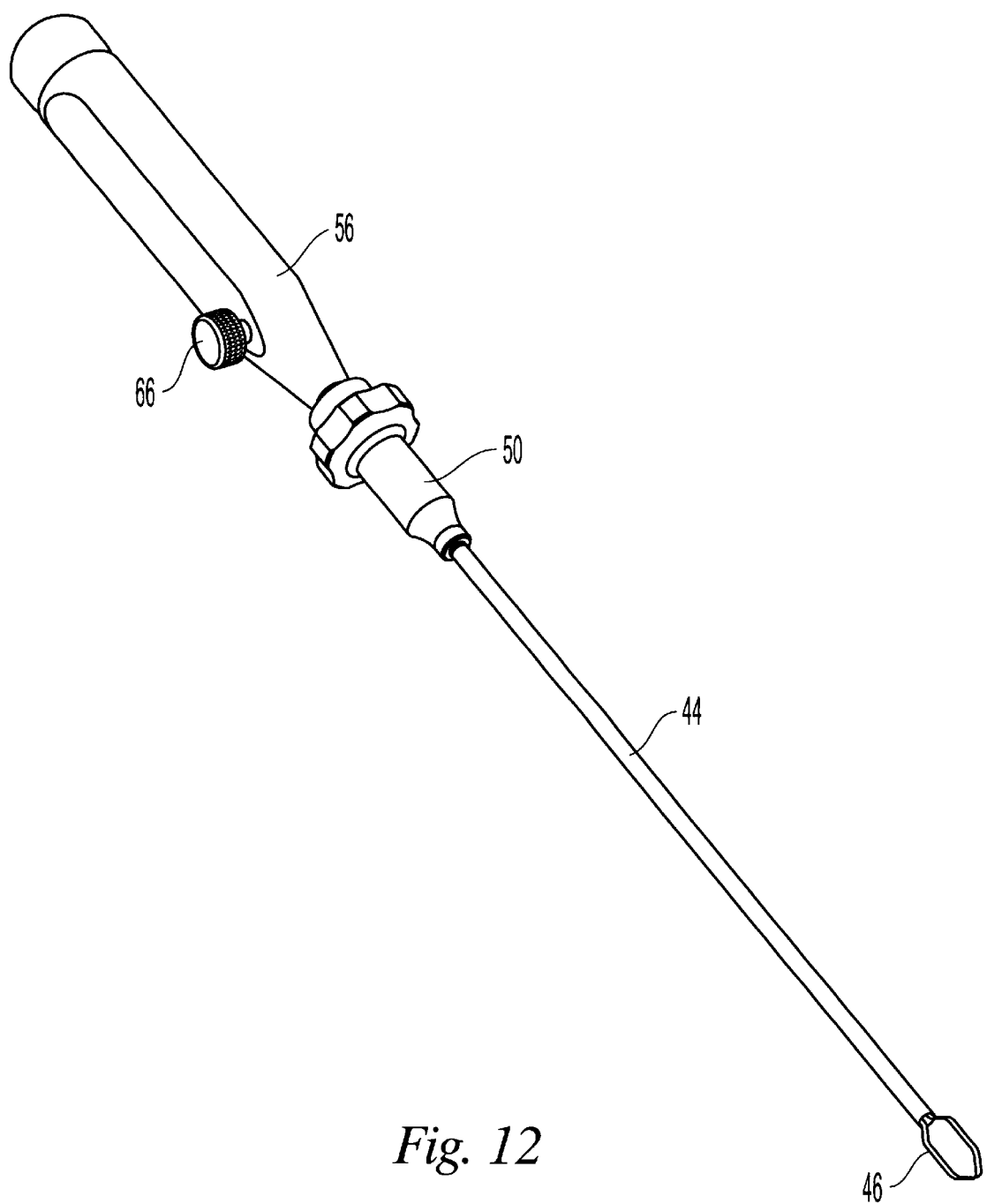
FIG. 12 is a view of a bone tamp of the memory metal ring embodiment.

The shape of the ring 46 is pre-set into the memory metal as is known in the industry. One such shape, shown in FIGS. 10A–C, is a rounded triangular shape. FIGS. 10A–C show how the ring 46 expands as it exits from the body 44. FIGS. 11A–D show another embodiment where the ring 46 is oval. FIG. 12 shows another embodiment of an expanding ring bone tamp. In this embodiment, the ring approximates a hexagonal shape.

Figure 13:
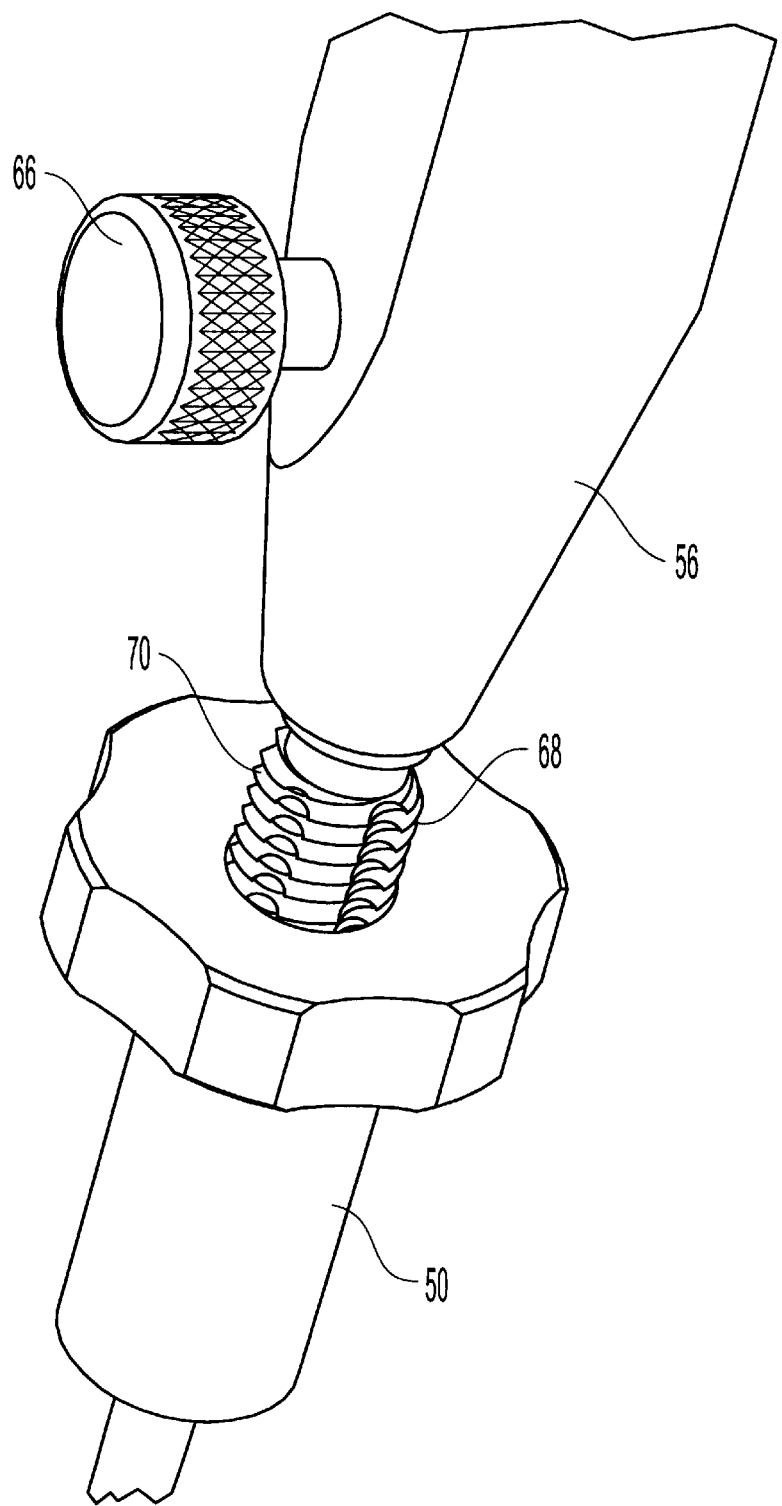
FIG. 13 is a view of a collar controlling mechanism with threads.

FIG. 13 is an embodiment of the collar 50 where collar movement is affected by rotating the collar on threads 68. The threads 68 advantageously have flat portions 70 made thereon such that the thread can be readily locked, or so that a spring-loaded bearing may make an audible click, as the collar is rotated and the bearing (not shown) passes over the flattened portions 70. The finer control given by threads allows for partial deployment of the tamping mechanism.

Figure 14:
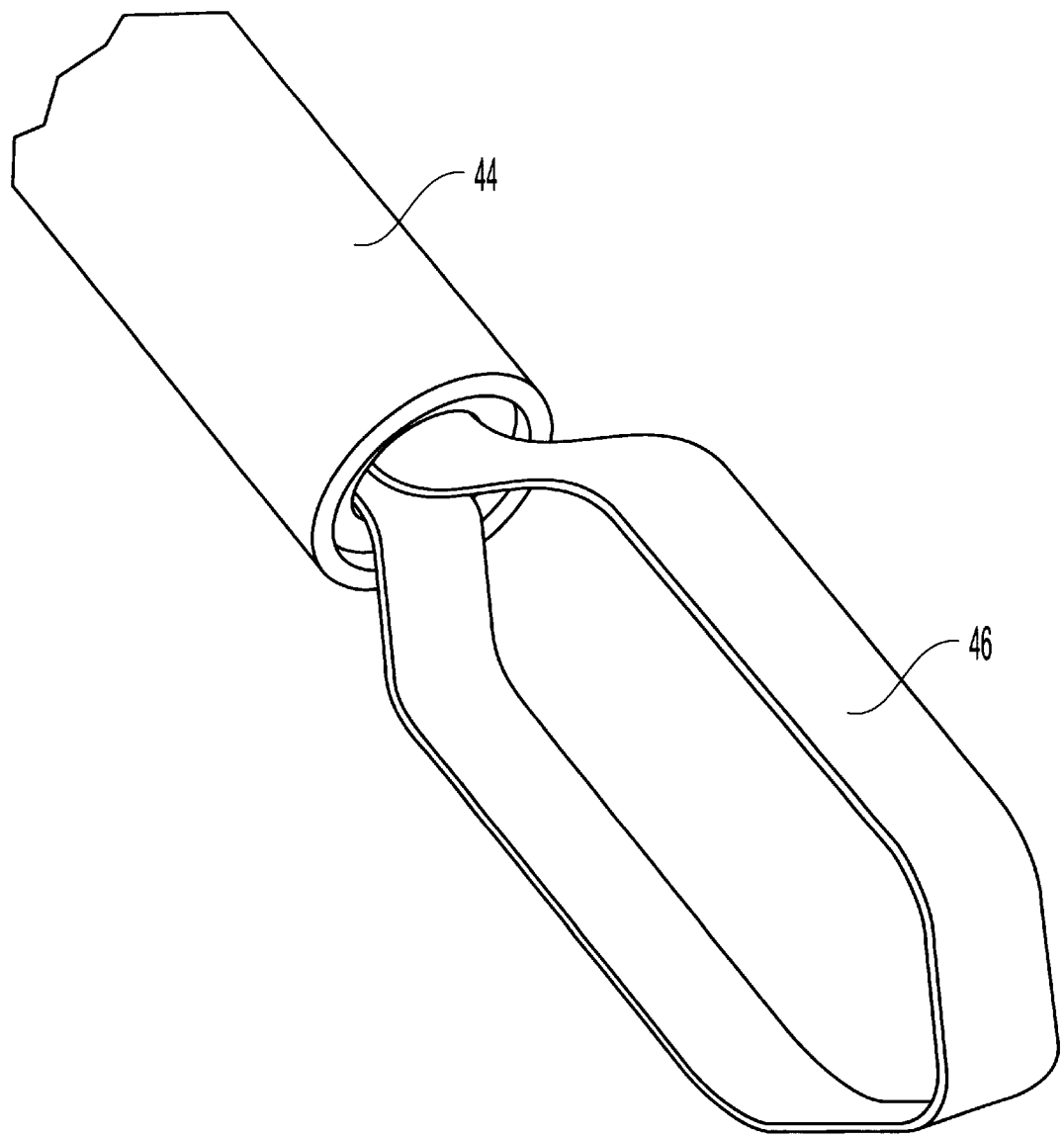
FIG. 14 is an expanded view of a memory metal ring.

FIG. 14 is a close-up view of the loop 46. In one embodiment, these loops are symmetrical. However, an asymmetric ring is used in another embodiment. In such an embodiment, shown in FIGS. 15A–C, one end of the material used to form the ring is supported at least partially by a rod 72 as it extends out of the body 44. The metal is then looped around to form a loop 46 and fed back through the body 44. Control of the deployment of the loop can be effected either by feeding and withdrawing the ribbon or, more preferably, by moving the body 44 relative to the rod 72. A groove (not shown) along the rod 72 passing back to the handle or along the body 44 allows the ribbon to be easily fed back to the collar or handle where it may be secured.

In each of these embodiments, the material used for the loop is a resilient material, such as a suitable steel or plastic. In an exemplary embodiment, a shape memory material, such as Nitinol, is used for the loop.

Figure 16B:
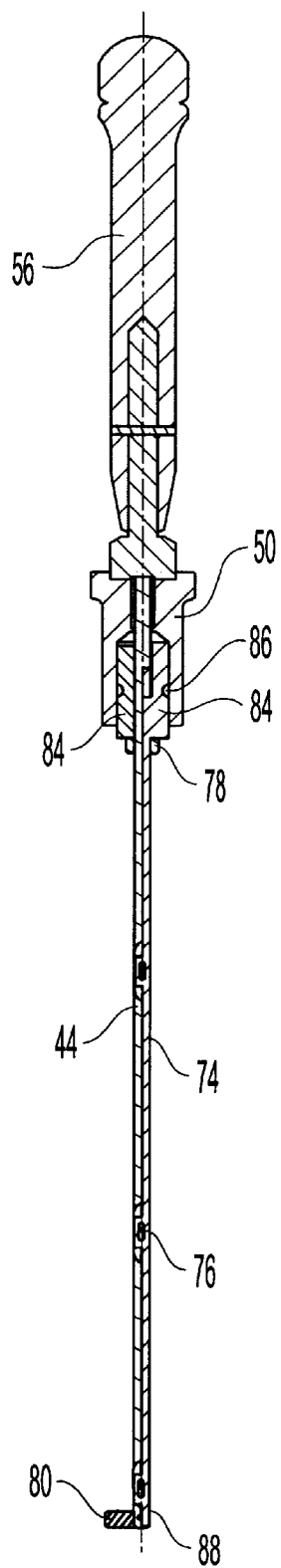
FIG. 16B is a cross-sectional view along the longitudinal axis of the bone tamp of FIG. 16A.
Figure 16A:
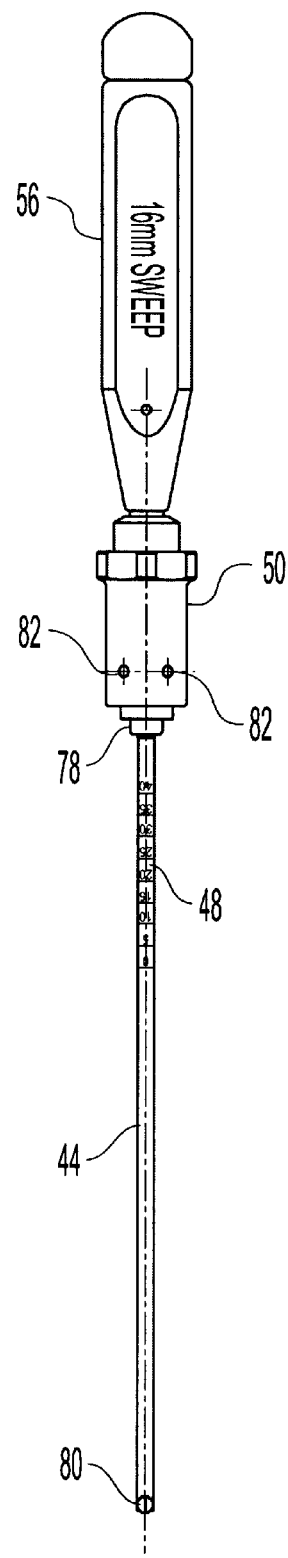
FIG. 16A is a view of a bone tamp of the flapper embodiment.

FIGS. 16A and 16B show a flapper embodiment of a bone tamp. This tamp has a collar 50 with threads 68. The body 44 of this embodiment has a groove cut therein where a rod 74 passes. If the rod 74 is not encased by the body 44 but just runs in an open groove, it is advantageous to have slidable tie-downs that positively hold the rod 74 against the body 44 in several pre-selected positions. There is a stop 78 that prevents the rod 74 from being over-extended. The rod 74 pushes the flapper 80. In FIGS. 16A and 16B, the rod is fully extended and the flapper is extended out of alignment with the body 44 by about 90 degrees. The set screws or bearings 82 hold the base 84 of the rod 74 withing the collar 50. There is a channel 86 in the base 84 which allows the collar to be rotated without rotating the body 44 or the rod 74. The flapper is held on by at least two points and a pin which form a hinge. In one embodiment, the range of motion of the flapper is gradually decreased as the collar is rotated in a direction to deploy the flapper. In another embodiment, the flapper has little range of motion at any time, but instead is gradually deployed as the collar is turned. One advantage of this embodiment is that a surgeon may gradually deploy the flapper and rotate the bone tamp so that the creation of the cavity is more gradual. With any of these embodiments, it is preferred that the flapper is held in its final position when the collar is fully deployed.

Figure 17:
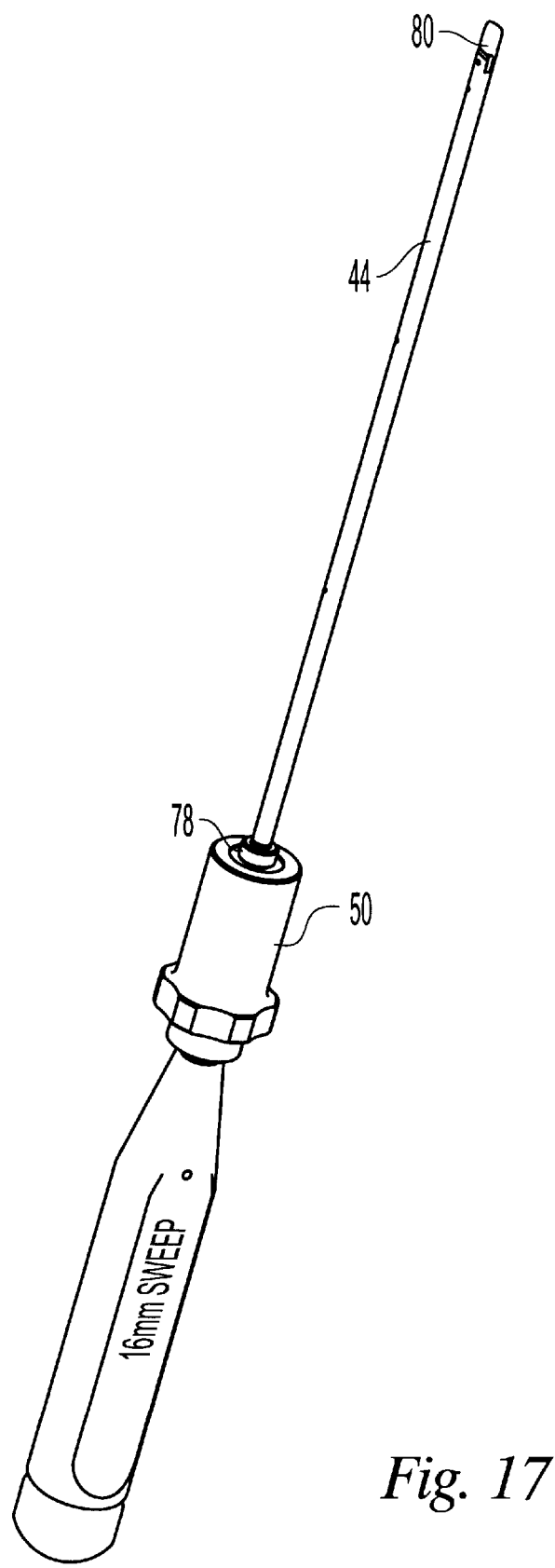
FIG. 17 is a view of a bone tamp of the flapper embodiment that is not deployed.
Figure 19:
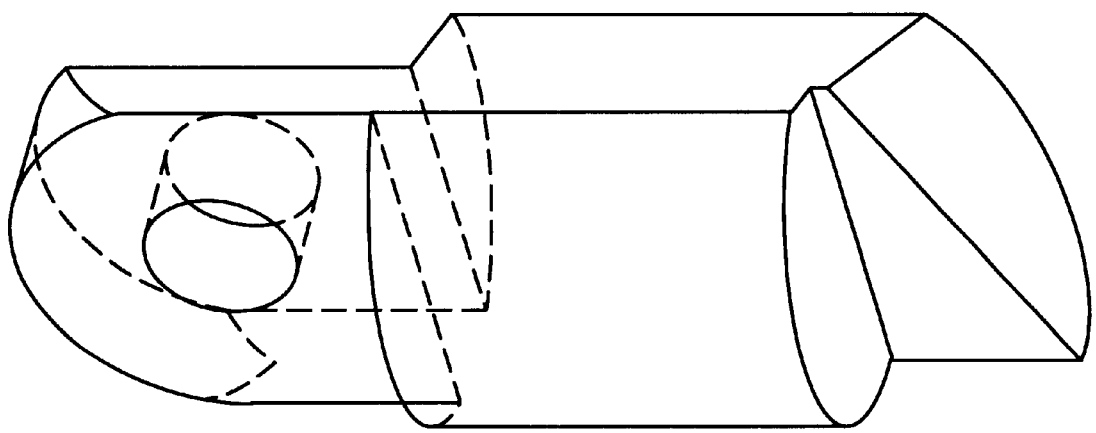
FIG. 19 is a view of details of a directional tip flapper.
Figure 20:
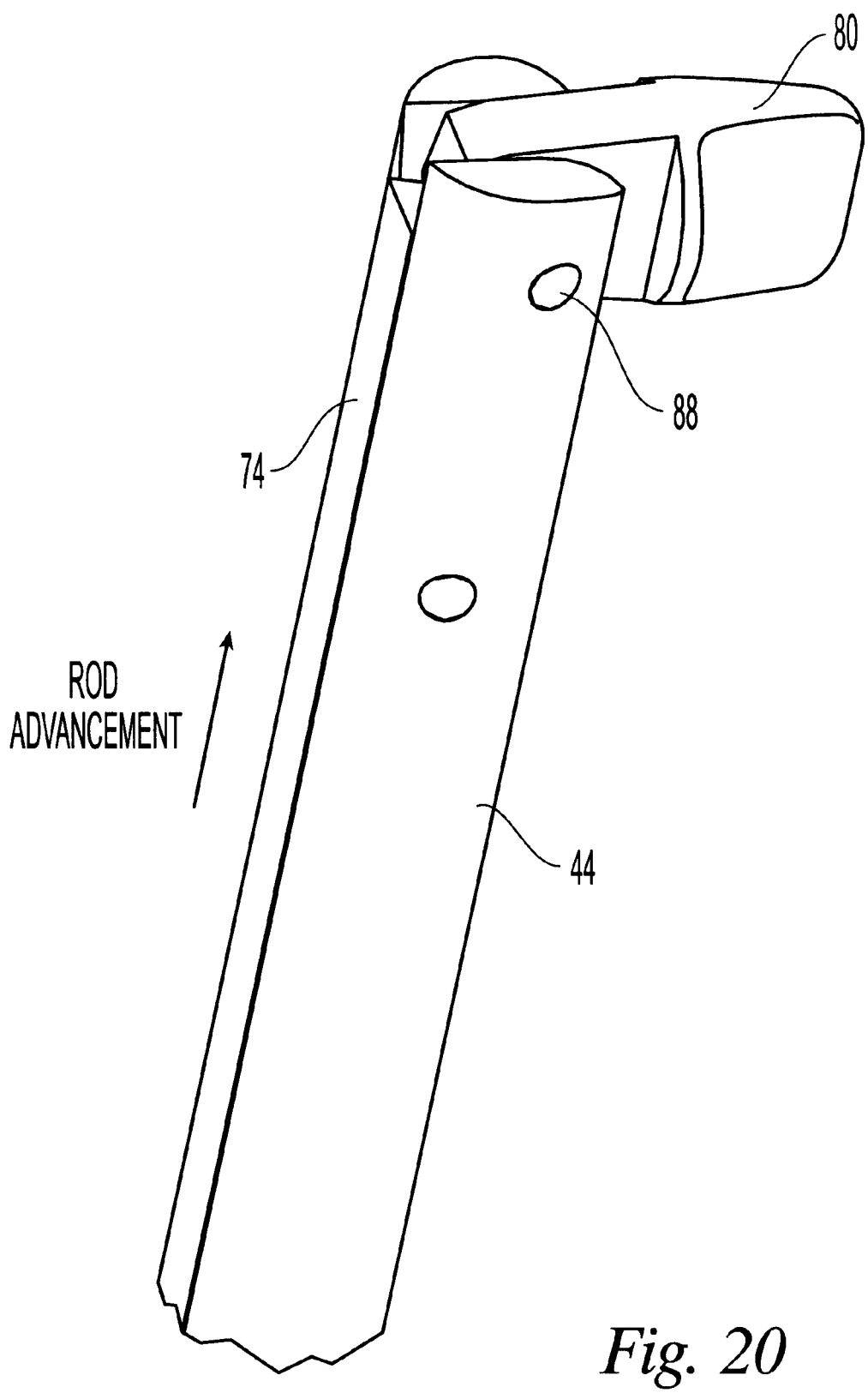
FIG. 20 is a view of the distal end of a bone tamp of the flapper embodiment that is fully deployed.

FIGS. 17–20 further illustrate the features of the flapper design described above. In FIG. 17 the collar 50 is well back from the stops 78. FIGS. 18A–E show details of the hinge 88 and blunted flapper 80. FIG. 19 shows a blow-up of a directional flapper 80, where rotating in one direction increases the tamping effect and rotating in the opposite direction increases erosion of the cancellous material. FIG. 20 more clearly shows one type of interaction between the rod 74 and the flapper 80, where the rod slides against and displaces the flapper.

Figure 21:
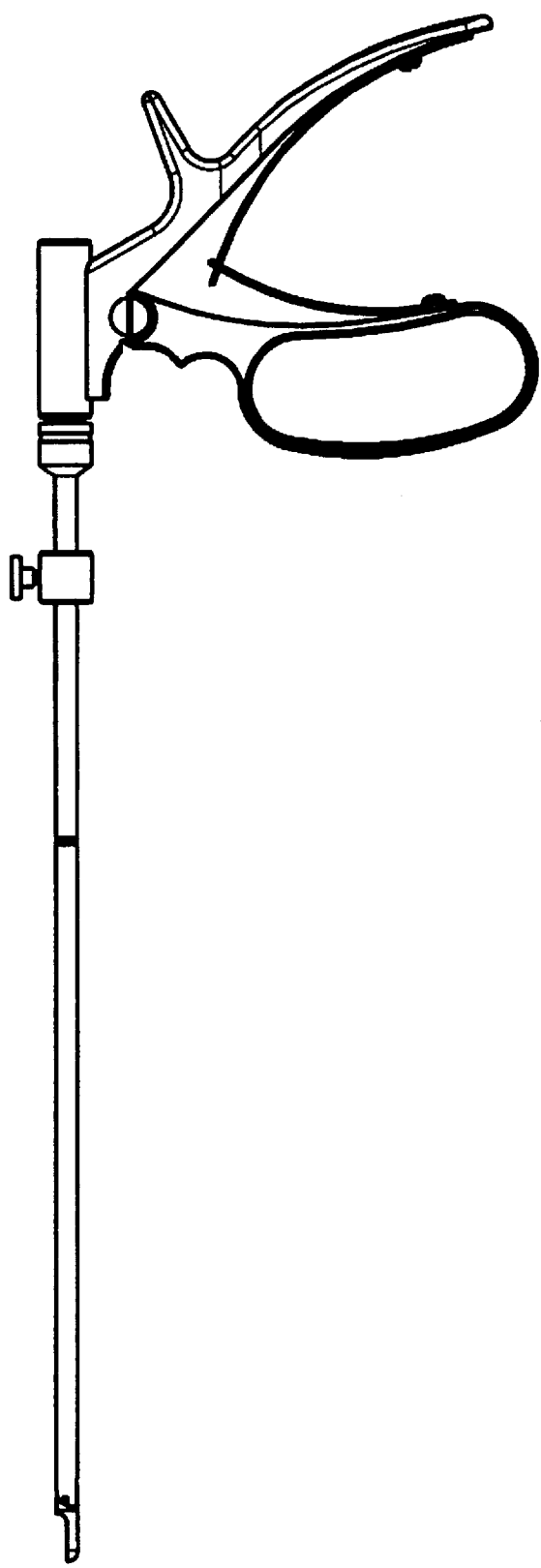
FIG. 21 is a view of a bone tamp of the flapper embodiment with a pistol-grip handle.
Figure 22:
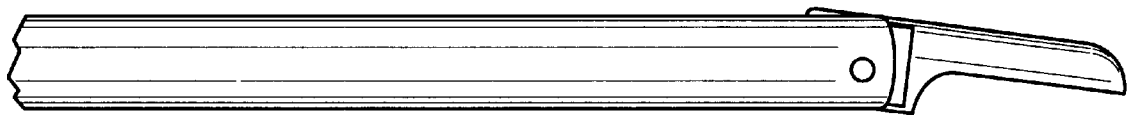
FIG. 22 is a view of a flapper only partially deployed.
Figure 23:
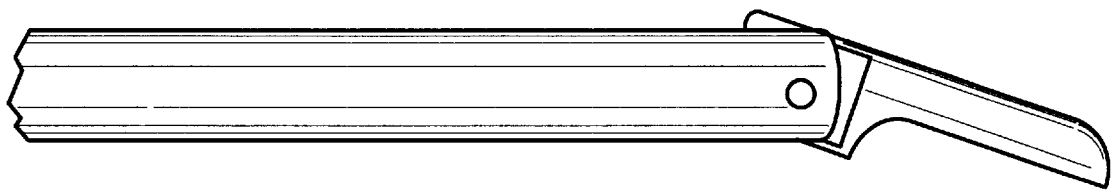
FIG. 23 is a view of a flapper only partially deployed.
Figure 24:
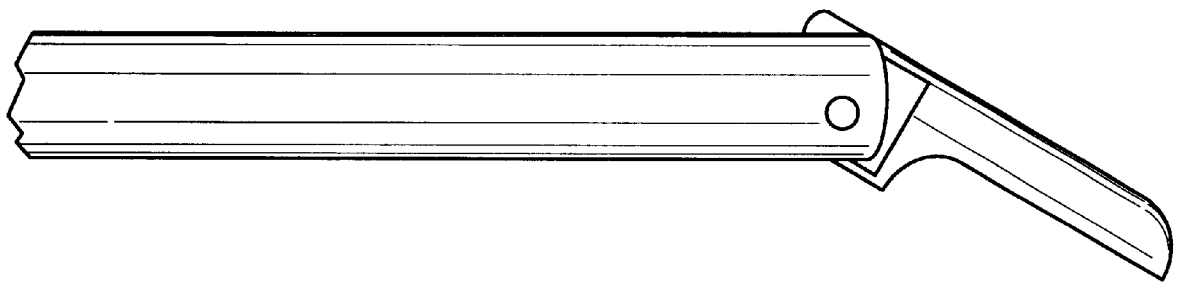
FIG. 24 is a view of a flapper only partially deployed.
Figure 25:
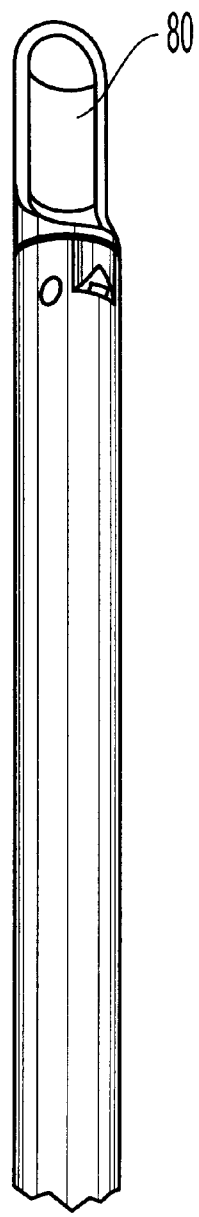
FIG. 25 is a view of a flapper that is not deployed.

FIG. 21 shows an embodiment of the flapper bone tamp in which the flapper deploys in response to squeezing a pistol-type grip, scissor-type grip, or any other grip having similar actuation. The control exhibited by the pistol-grip controlling mechanism, shown in FIGS. 22–24, is such that the flapper can be partially or fully deployed depending on the amount of travel of the arms of the pistol-grip. FIG. 25 shows the flapper in its un-deployed position.

Figure 26B:
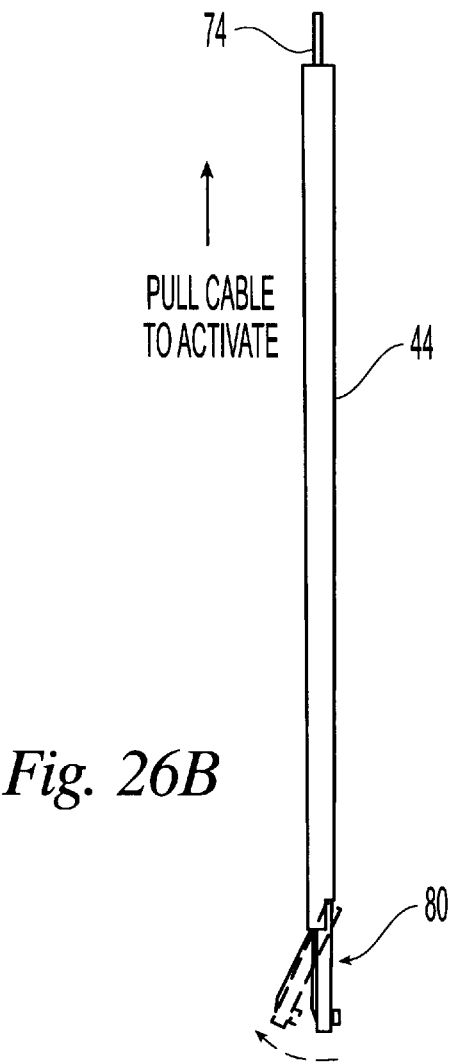
FIGS. 26A–C are three views of a bone tamp of the flapper embodiment.
Figure 26C:
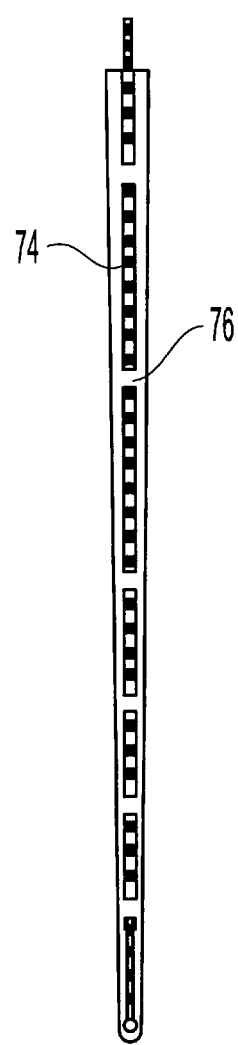
Figure 26A:
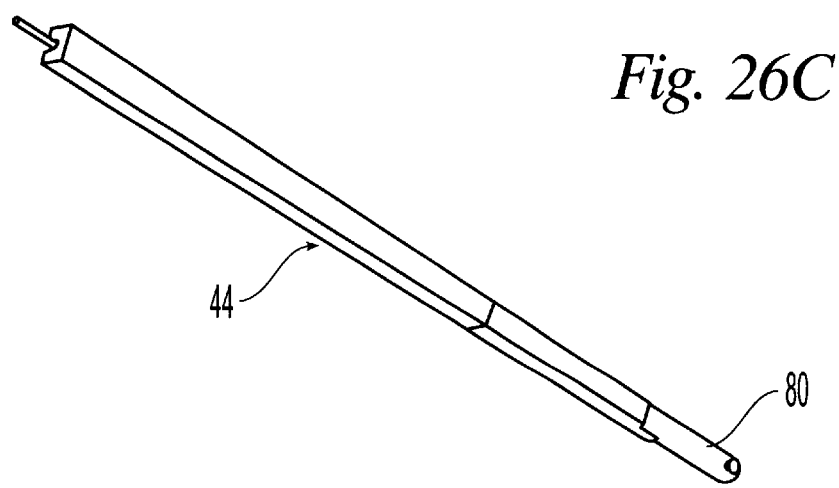
Figures 27A, 27B, 27C, 27D, 27E, 27F:
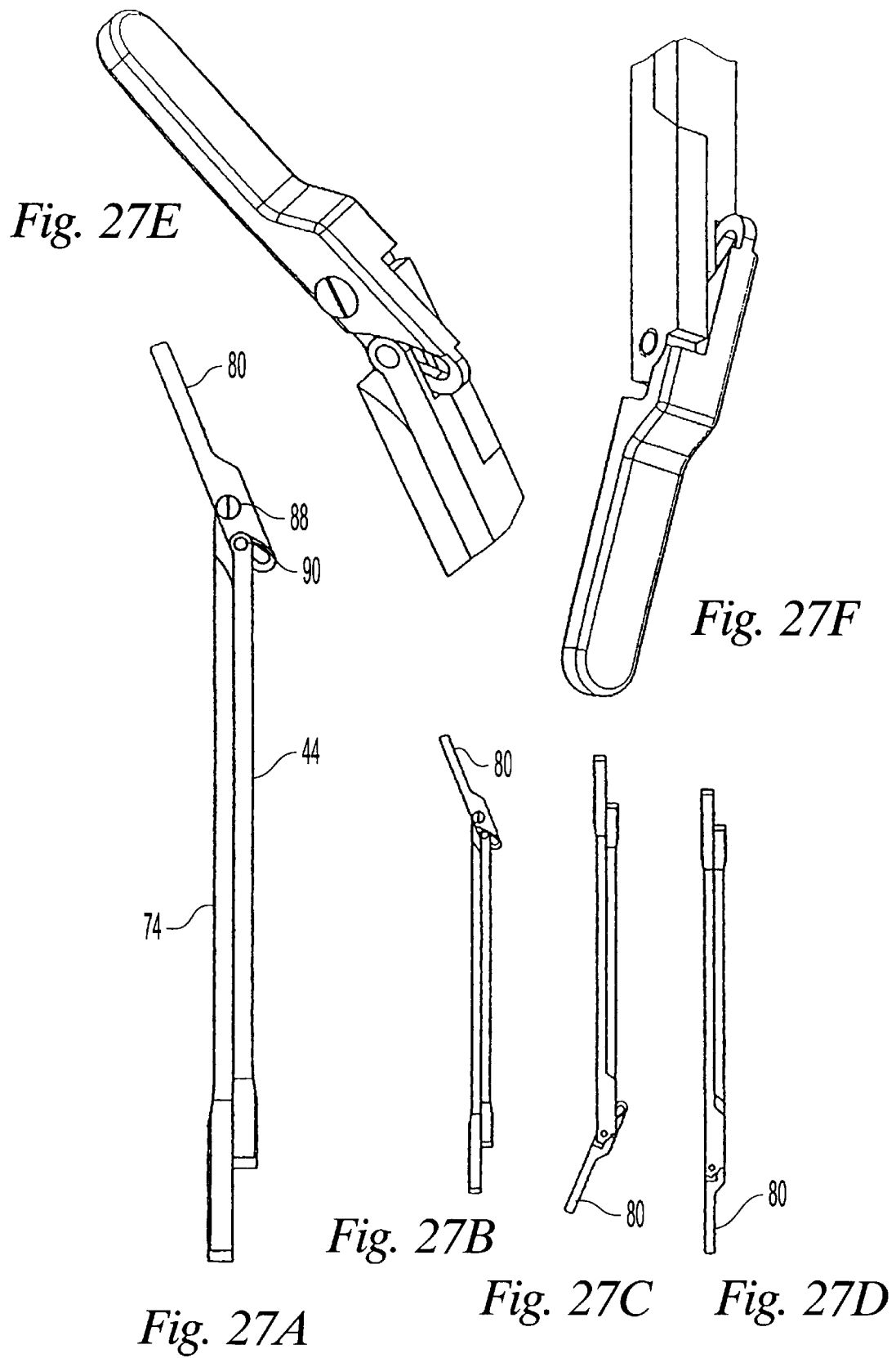
FIGS. 27A–F are six views of a bone tamp of the flapper embodiment.

FIG. 26 shows an embodiment of the flapper tamp wherein pulling a metal or plastic wire attached directly to the flapper causes the flapper to move out of alignment with the shaft.

FIGS. 27A–F show another embodiment of the flapper bone tamp. In this embodiment, the opposite end of the flapper is slidingly engaged at point 90 to the body 44, as well as being hinged at point 88.

Threaded Syringe

Figure 28:
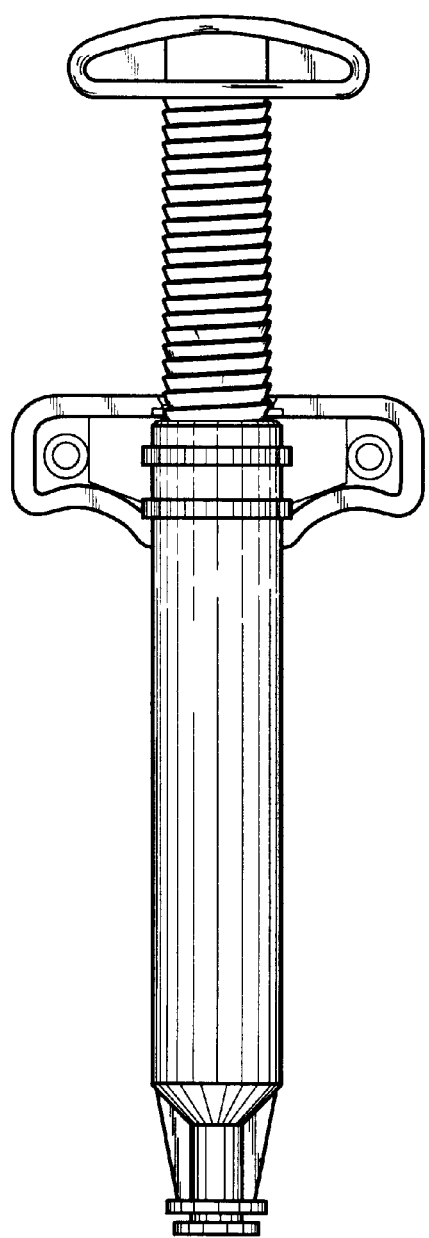
FIG. 28 is a view of a syringe-type device for displacing materials through the cannula.

FIG. 28 shows a syringe adapted to fit a tube which is extendable through the cannula. In addition to the description that follows, the syringe is further described in pending U.S. patent application Ser. No. 09/932,313, filed on Aug. 20, 2001 and entitled "Threaded Syringe for Delivery of a Bone Substitute Material" (attorney docket 8932-273), which is incorporated by reference herein in its entirety. The syringe is adapted to deliver material as necessary for treatment of the formed cavity. In some embodiments between about 100 psi and about 1500 psi must be generated to inject the treatment material at a sufficient rate. The syringe is advantageously threaded so that turning the threaded portion results in displacement of a plunger and resultant controlled high pressure delivery of material. This structure allows the syringe to deliver the material in a controlled and discrete fashion at a desired pressure.

Examples of the delivered material include polymethylmethacrylate (PMMA) or any other bone filler material. In a preferred embodiment, the bone filler material is a composition comprising calcium phosphate, such as provided by Norian Corporation, 10260 Bubb Road, Cupertino, Calif. 95014. Further information regarding examples of such compositions is available in the following U.S. patents that are incorporated by reference herein: U.S. Pat. Nos. 5,336,264, 5,962,028, 5,820,632, 6,005,162, 5,900,254, 6,002,065, 5,782,971, and 5,952,010. Additional examples of bone filler material that may be used with the present invention can be obtained from the following U.S. patents, which are also incorporated by reference: U.S. Pat. Nos. 5,129,905, 5,047,031, 4,880,610, 5,053,212, and 5,178,845.

Figure 29B:
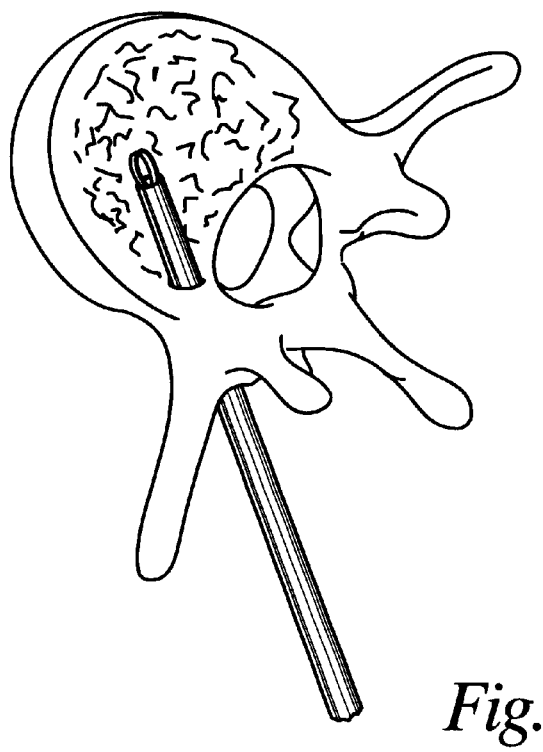
FIGS. 29A and 29B are two views of a bone tamp of the memory metal ring embodiment as it would appear in a vertebra.
Figure 29A:
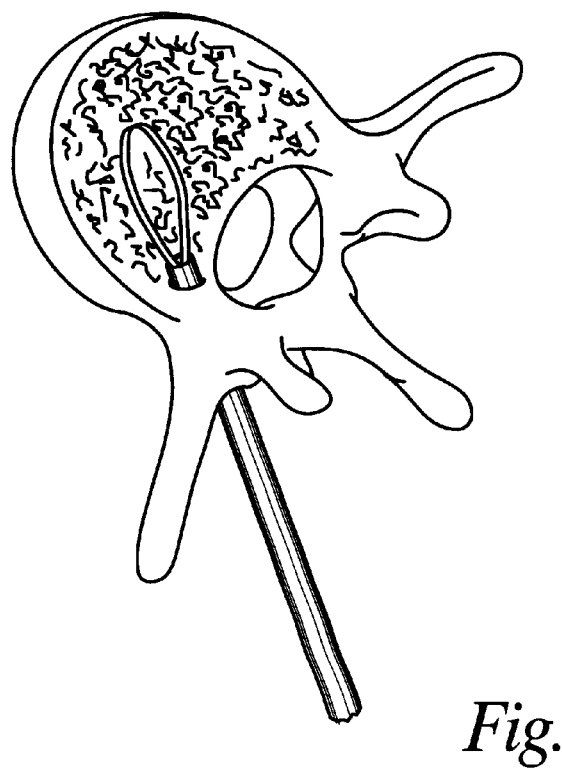

FIG. 29 shows the deployment of a ring-type bone tamp with the ring made of a shape memory metal. The releasing of the ring corresponds to withdrawing of the body partially from the cancellous area.

Figure 30:
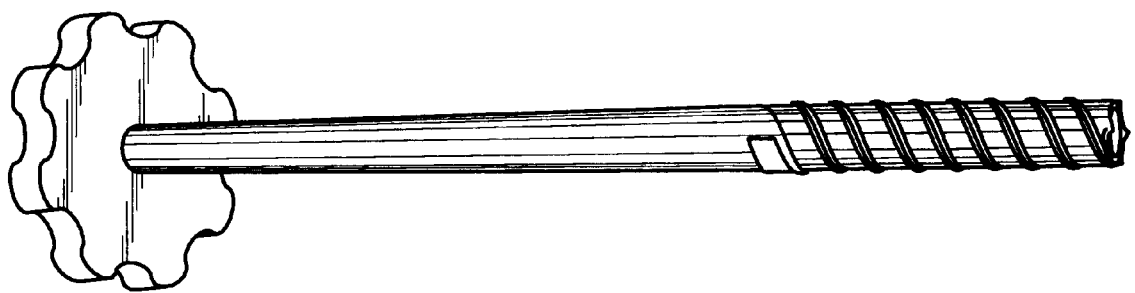
FIG. 30 is a view of a threaded cannula with an aggressive cutting tip.

FIG. 30 shows a threaded cannula, where the threads are raised from the body to assist in axially moving the cannula through bone. As shown in FIG. 30, the tip of the cannula may have an aggressive cutting edge to assist in properly positioning the cannula in the bone. The aggressive tip may include sharp protrusions that can cut or grind bone. Alternatively, as shown in FIG. 7C, the cannula may have a less aggressive tip. For instance, the tip may have a circular profile. The edge of the tip of the cannula may be beveled, rounded, blunt, or any other shape to achieve a desired performance or feel. Beveling the edge of the tip, for instance, may allow the tip to have a sharp edge in order to better cut through the bone, or may provide a better sense of control or feel for the surgeon.

In addition, the tip of the cannula may have other shapes to achieve a desired functionality or feel. For example, the tip may be wedge-shaped so that the leading edge of the tip may assist in piercing the bone with less rotational force in passing through the skin.

Of course, the smaller diameter the tools, the less damage is made during entry. These tools have small diameter—for example, the bone tamps most preferably have an outer diameter in the body of between about 4 mm and about 6 mm. The cannula has an outer diameter that is typically at least about 1 mm greater than this. Size is therefore very important in view of inadvertent damage during ingress and egress of the tools.

In use, the bone tamp body 44 may be used for axial and rotational movement within a cannula 34. The physician is able to freely slide the body 44 axially within the guide sheath of the cannula body 34. As a secondary precaution, when fully confined by the cannula, the loop structure, if projecting a significant distance beyond the distal end of the bone tamp body, is collapsed by the surrounding cannula.

During normal operation, the body of the bone tamp collapses the memory metal ring structure. When free of the body of the bone tamp, the loop structure springs open to assume its normal dimension. The physician can operate the collar 50 to alter the dimension of the ring 46 at will.

The physician is also able to rotate the deployed loop structure by rotating the handle. Rotation of the loop structure tamps back, and to some extent slices through surrounding tissue mass. Rotation is preferably manual, as tamping the bone requires better "feel" than does simply cutting away tissue.

The tool is particularly useful for, but is not limited in its application to, vertebrae. The tools can be deployed equally as well in long bones and other bone types.

The vertebra includes a vertebral body, which extends on the anterior side of the vertebra. The vertebral body includes an exterior formed from compact cortical bone. The cortical bone encloses an interior volume of reticulated cancellous, or spongy, bone (also called medullary bone or trabecular bone).

The vertebral body is generally in the shape of an oval disk. Access to the interior volume of the vertebral body can be achieved, for example, by wedging and/or cutting through hard bone. Such wedging and/or cutting can be achieved, for example, with a probe and cannula as described here.

When the bone tamp is deployed outside the cannula in the cancellous bone, the physician operates the controlling mechanism in the manner previously described to obtain a desired dimension for the loop structure or the desired deployment of the flapper. The physician manually rotates the loop structure or flapper through surrounding cancellous bone. The rotating structure cuts and tamps back cancellous bone and thereby forms a cavity. Synchronous rotation and operation of the controlling mechanism to enlarge the dimensions of the tamping structure during the procedure allows the physician to achieve a create a cavity of desired dimension.

The procedure for use of these tools is as follows. First, the probe is constructed with the probe tip extending beyond the probe body by a predetermined length. The handle is attached to the probe. Alternatively, the cannula is preloaded around the probe if the handle on the probe is non-removable. The probe is advanced through the bone, i.e., vertebral body, preferably through percutaneous approach to the desired depth. The handle is removed, leaving the probe body in place, and the cannula is slipped over the probe (if it has not been preloaded thereon). The depth markings may be used to determine the depth of penetration. The cannula is advanced down the probe shaft and is threaded or worked into the pedicle or vertebral body.

Then, the probe is removed while the cannula remains in place. If previously detached, the probe handle may be reattached to facilitate removal of the probe. The bone tamp is inserted through the cannula and then the tamping mechanism is deployed therein, with appropriate retraction of the deployment and/or rotation as needed, to create the void space. When the cavity is of the desired shape and size, the tamping mechanism is retracted so that the bone tamp can be withdrawn through the cannula.

Then, optionally, a void filler is placed into the cavity via the cannula using the syringe of FIG. 28 or any other suitable device. The displacement rod may be used at any time to make sure the body of the cannula remains clean and obstruction-free, and also may be used to displace treatment material that adheres to the cannula into the cavity. Finally, the cannula is removed.

Another optional step in the process described herein is to deliver medicament to the treated area. The medicament may include, for example, sealants, anticoagulants, coagulants, analgesics or pain relievers, growth factors, or antibiotics. The delivery of the medicament to the treated area may take place at any time desired by the physician, but it is preferred that the medicament is delivered before the cavity is filled. The delivery of the medicament may be accomplished in any manner desired by the physician. Some methods of delivery include spray coating an inflatable device and placing it inside the cavity, injecting the medicament inside the cavity through the cannula, or spray coating the interior of the cavity. In one embodiment, the inflatable device has at least two layers of material with a medicament disposed between the layers. The outermost layer can be removed or break down so that the medicament can be released.

An inflatable device can also be used to deliver a reactive composition. For instance, one compound can be disposed between two layers of the device and the outermost layer can be covered with another compound. As the outermost layer is removed or breaks down, the two compounds intermix and react. In an alternative embodiment, the compounds can be disposed between different layers of the inflatable device. In this embodiment, the outermost layer of the inflatable device is removed or breaks down so that a first compound is released. Then, the next layer of the inflatable device is removed or breaks down to release a second compound. In yet another embodiment, an intermediate layer of the inflatable device can be removed or broken down before the outermost layer is removed or broken down. Any or all of the compounds may also assist in inflating the inflatable device.

Several of these and other methods for delivering a medicament to the cavity are described in pending U.S. application Ser. No. 09/908,899, which has been incorporated by reference in its entirety. Additionally, the tools described herein may be utilized to deliver the medicament. For example, the flapper tip may be configured and adapted to spray or otherwise deliver the medicament to the cavity. The medicament may be supplied to the flapper tip through a channel, tube, or any other manner from a supply of medicament outside of the patient. The supply of medicament may be from a reservoir within the tool itself or may be supplied from another source.

A single use of any one of the tools creates contact with surrounding cortical and cancellous bone. This contact can damage the tools, creating localized regions of weakness, which may escape detection. In addition, exposure to blood and tissue during a single use can entrap biological components on or within the tools. The tools described here allow for replacement of each component, and especially easy replacement of those components which contact bone. The tools also are easy to clean and disassemble. The tools may be used only once and then discarded. If so, use of plastics is preferred for many tool structures.

In another embodiment, the tools described herein may be used to restore bone. The restoration of bone may be performed as an additional step in the methods described above, or may be performed without creating a cavity inside the bone. Once the cannula is positioned to provide access to the interior of the bone, a tool may be placed in the interior region of the bone and deployed to lift or restore collapsed, fractured, or weakened bone. In one example of this method the flapper of the tools described herein is extended so that the tip contacts the bony surface to be restored. The physician then manipulates the tool so that the flapper applies pressure to the bone in order to restore it.

Other types of tools also may be used to restore bone. For instance, the loop design described herein may be modified to have a plurality of loops that, when deployed, expand outward until at least one loop contacts the surface to be restored. Again, the physician may then further manipulate the tool, such as by rotating it, moving it axially, or further deploying the loops, so that pressure is applied to the treated surface of the bone. Any other tool or material that expands to restore the bone may be equally suitable. In one example, the expanding tip may be designed and constructed to remain within the bone to provide long-term support for the treated area of bone.

In another example, hydrogel may be inserted into the interior of the bone near the area to be restored. In one embodiment, the flapper tip of the bone tamp may be made of hydrogel so that the tip can be used to reduce bone after it has been used to create a cavity. As the hydrogel absorbs water, it expands until it reaches the portion of the bone to be restored. Thereafter, further expansion of the hydrogel will cause the bone to be lifted, or restored toward its natural anatomy. Bone filler material may be inserted into the hydrogel to provide support. Alternatively, the hydrogel may be allowed to expand and harden without the support of bone filler material.

While it is apparent that the invention disclosed herein is well calculated to fulfill the objects stated above, it will be appreciated that numerous modifications and embodiments may be devised by those skilled in the art. Therefore, one skilled in the art would appreciate that such modifications and embodiments fall within the true spirit and scope of the present invention.

We claim:

1. A surgical instrument having a longitudinal axis for creating a cavity in bone, comprising:
    first and second members having proximal and distal ends,
    a tip having proximal and distal ends for creating a cavity in bone, and
    a fastening element for securing the tip to the first member,
    the first member, the tip, and the fastening element forming a joint,
    wherein the joint is operatively associated with the second member to provide a first mode allowing the joint to articulate freely between an initial position and a fully deployed position, a second mode that substantially immobilizes the joint in the fully deployed position, and a third mode, wherein the second member blocks the tip from articulating freely between the initial position and the fully deployed position.

2. The device of claim 1, wherein the third mode allows the joint to articulate freely between at least one intermediate position and the fully deployed position.

3. The device of claim 1, further comprising a collar located between the handle and the tip.

4. The device of claim 3, wherein the collar is operably associated with the tip to articulate the joint.

5. The device of claim 4, wherein the collar is operably associated with the tip to lock the joint.

6. The device of claim 5, wherein the collar is operably associated with the tip to unlock the joint.

7. The device of claim 3, wherein the third mode allows the joint to articulate freely between at least one intermediate position and the fully deployed position.

8. The device of claim 7, wherein the at least one intermediate position and the fully deployed position define a range of free motion, and the collar is operably associated with the joint to selectively define the at least one intermediate position.

9. The device of claim 8, wherein rotating the collar in one direction decreases the range of free motion.

10. The device of claim 9, wherein rotating the collar through a range of motion decreases the free range of motion of the tip by a related amount.

11. The device of claim 10, wherein the related amount is proportional to the range of motion of the collar.

12. The device of claim 11, wherein the related amount is directly proportional to the range of motion of the collar.

13. The device of claim 12, wherein rotating the collar in the opposite direction increases the range of free motion.

14. The device of claim 13, wherein the collar is operable between a first position and a second position, such that when the collar is in the first position the tip is in the initial position, and when the collar is in the second position the tip is in the fully deployed position.

15. The device of claim 14, wherein the collar is operable between the first and second positions and at least one third position, such that when the collar is in the at least one third position the tip is in the at least one intermediate position.

16. The device of claim 1, further comprising a handle adjoining the proximal end of the first member.

17. The device of claim 16, wherein the handle comprises a surface defining a first plane.

18. The device of claim 17, wherein the joint articulates in a second plane.

19. The device of claim 18, wherein the first plane is different from the second plane.

20. The device of claim 19, wherein the first and second planes are orthogonal.

21. The device of claim 16, wherein the handle is fixed to the first member.

22. The device of claim 1, wherein the distal end of the tip comprises a plurality of surfaces.

23. The device of claim 22, wherein the distal end of the tip is substantially symmetrical.

24. The device of claim 23, wherein the distal end of the tip is substantially blunt.

25. The device of claim 1, wherein the tip is adapted to create a cavity in bone when the tip is inserted into bone and rotated about the longitudinal axis of the device.

26. The device of claim 25, wherein the tip comprises a bore for receiving the fastening element.

27. The device of claim 26, wherein the proximal end of tip is seated within the distal end of the first member.

28. The device of claim 1, wherein the second member is selectively movable from a first position to a second position.

29. The device of claim 28, wherein the second member is capable of displacing the proximal end of the tip to articulate the joint.

30. The device of claim 28, wherein the second member is not positively connected to the tip.

31. The device of claim 28, wherein the second member is of blocking articulation of the joint.

* * * * *